(12) United States Patent
Yamato et al.

(10) Patent No.: US 9,097,689 B2
(45) Date of Patent: Aug. 4, 2015

(54) THROUGHPUT INFORMATION GENERATING APPARATUS OF SAMPLE ANALYZER, SAMPLE ANALYZER, THROUGHPUT INFORMATION GENERATING METHOD OF SAMPLE ANALYZER, AND COMPUTER PROGRAM PRODUCT

(75) Inventors: Takashi Yamato, Kakogawa (JP); Hisashi Nakatsuka, Kobe (JP); Hiroshi Kurono, Kobe (JP)

(73) Assignee: SYSMEX CORPORATION, Kobi-shi, Hyogo (JP)

( * ) Notice: Subject to any disclaimer, the term of this patent is extended or adjusted under 35 U.S.C. 154(b) by 925 days.

(21) Appl. No.: 13/171,914

(22) Filed: Jun. 29, 2011

(65) Prior Publication Data
US 2012/0004857 A1 Jan. 5, 2012

(30) Foreign Application Priority Data

Jun. 30, 2010 (JP) .................. 2010-148640
Mar. 10, 2011 (JP) .................. 2011-053457

(51) Int. Cl.
G06F 19/00 (2011.01)
G01N 33/49 (2006.01)
G01N 35/00 (2006.01)

(52) U.S. Cl.
CPC .... *G01N 35/0092* (2013.01); *G01N 2035/0094* (2013.01); *Y10T 436/11* (2015.01); *Y10T 436/113332* (2015.01); *Y10T 436/114165* (2015.01); *Y10T 436/114998* (2015.01)

(58) Field of Classification Search
CPC ............. G01N 35/0092; G01N 2035/0094; Y10T 436/11; Y10T 436/113332; Y10T 436/114165; Y10T 436/114998
See application file for complete search history.

(56) References Cited

U.S. PATENT DOCUMENTS 6,022,746 A    2/2000 Fritchie et al.
6,096,561 A *  8/2000 Tayi .............................. 436/518
(Continued)

FOREIGN PATENT DOCUMENTS

EP    1881329 A2    1/2008
JP    06-109743     4/1994
(Continued)

OTHER PUBLICATIONS

Corkan, Andrew L. et al., "Experiment manager software for an automated chemistry workstation, including a scheduler for parallel experimentation," Chemometrics and Intelligent Laboratory Systems, Oct. 1992, No. 1, Amsterdam, NE, Elsevier, pp. 47-74.
(Continued)

*Primary Examiner* — Mohamed Charioui
*Assistant Examiner* — John Kuan
(74) *Attorney, Agent, or Firm* — Brinks Gilson & Lione

(57) ABSTRACT

An apparatus for generating throughput information of a sample analyzer is disclosed. Specifically, this apparatus generates throughput information of a sample analyzer capable of measuring a sample on a plurality of measurement items in which measurement time differs from each other. The apparatus receives an input of a plurality of measurement orders, wherein a measurement order includes a designation of at least one measurement item, generates the throughput information of the sample analyzer based on the received plurality of measurement orders; and outputs the generated throughput information.

6 Claims, 23 Drawing Sheets

(56) References Cited

U.S. PATENT DOCUMENTS

| | | |
|---|---|---|
| 6,594,537 B1 | 7/2003 | Bernstein et al. |
| 8,343,423 B2 | 1/2013 | Mori et al. |
| 2002/0116132 A1 | 8/2002 | Rhett et al. |
| 2004/0202577 A1 | 10/2004 | McNeil et al. |
| 2006/0178776 A1 | 8/2006 | Feingold et al. |
| 2008/0020469 A1* | 1/2008 | Barnes et al. ............ 436/46 |
| 2008/0312893 A1* | 12/2008 | Denton ................... 703/11 |
| 2009/0081794 A1 | 3/2009 | Wakamiya et al. |
| 2010/0101339 A1* | 4/2010 | Tatsutani et al. ........ 73/863.91 |

FOREIGN PATENT DOCUMENTS

| | | |
|---|---|---|
| JP | 9-34731 A | 2/1997 |
| JP | 2002-156380 A | 5/2002 |
| JP | 2005-30762 A | 2/2005 |
| JP | 2009-204409 A | 9/2009 |

OTHER PUBLICATIONS

Extended European Search Report for European Application No. 11171890.4, dated Sep. 23, 2011, 11 pages.

\* cited by examiner

FIG. 21

| | C401 | C402 | C403 | C404 | C405 | C406 | C407 | C408 |
|---|---|---|---|---|---|---|---|---|
| | | | | | | | MOF | |
| | | | 16022 | 15070 | 15120 | 12500 | 12550 | 10520 |
| | SAMPLE ID | ARRIVAL TIME | PT THS | APTT FSL | FIBRINOGEN | BC ANTITHROMBIN III | BC PLASMONOGEN | BC PROTEIN C |
| | Test1 | 9:00 | * | | | | | |
| | Test2 | 9:01 | * | * | | | | |
| | Test3 | 9:02 | * | * | | | | |
| | Test4 | 9:03 | * | * | | | | |
| | Test5 | 9:04 | * | | | | | |
| | Test6 | 9:05 | * | | | | | |
| | Test7 | 9:06 | * | * | | | | |
| | Test8 | 9:07 | * | | | | | |
| | Test9 | 9:08 | * | | | | | |
| | Test10 | 9:09 | * | | | | | |
| | Test11 | 10:00 | * | | | | | |
| | Test12 | 10:00 | * | | | | | |
| | Test13 | 10:00 | * | | | | | |
| | Test14 | 10:00 | * | | | | | |
| | Test15 | 10:00 | * | | | | | |
| | Test16 | 10:00 | * | | | | | |
| | Test17 | 10:00 | * | | | | | |
| | Test18 | 10:00 | * | * | | | | |
| | Test19 | 10:00 | * | | | | | |
| | Test20 | 10:00 | * | | | | | |
| | Test21 | 10:00 | * | | | | | |
| | Test22 | 10:00 | * | | | | | |
| | Test23 | 10:00 | * | | | | | |
| | Test24 | 10:00 | * | * | | | | |
| | Test25 | 10:00 | * | | | | | |
| | Test26 | 11:00 | * | | | | | |
| | Test27 | 11:00 | * | * | | | | |
| | Test28 | 11:00 | * | | | | | |
| | Test29 | 11:00 | * | | | | | |
| | Test30 | 12:00 | * | | | | | |
| | ... | ... | ... | ... | ... | ... | ... | ... |

THROUGHPUT INFORMATION GENERATING APPARATUS OF SAMPLE ANALYZER, SAMPLE ANALYZER, THROUGHPUT INFORMATION GENERATING METHOD OF SAMPLE ANALYZER, AND COMPUTER PROGRAM PRODUCT

RELATED APPLICATIONS

This application claims priority under 35 U.S.C. §119 to Japanese Patent Application Nos. 2010-148640 filed on Jun. 30, 2010 and 2011-053457 filed on Mar. 10, 2011, the entire content of which is hereby incorporated by reference.

BACKGROUND OF THE INVENTION

1. Field of the Invention

The present invention relates to a throughput information generating apparatus for generating throughput information indicating the throughput of the sample analyzer for analyzing samples such as blood and urine, a sample analyzer, a throughput information generating method of the sample analyzer, and a computer program for causing a computer to generate the throughput information of the sample analyzer.

2. Description of the Related Art

When introducing the sample analyzer to facilities such as hospitals and inspection centers, an user of the facility determines the model of the sample analyzer, the number of apparatuses to introduce, the operation method of the sample analyzer in the inspection task, or the like with reference to the throughput of the sample analyzer. Thus, the number of tests per unit time is normally disclosed in the catalogue of the sample analyzer as an index indicating the throughput.

In sample test, the time required for the measurement of the sample may differ depending on the measurement item as with the blood coagulation measurement. In the sample analyzer for carrying out such type of test, a configuration in which a plurality of samples divided into cuvettes is processed in parallel is adopted (see e.g., Japanese Laid-Open Patent Publication No. 6-109743), but the number of tests per unit time differs depending on kind of measurement item being tested. Furthermore, frequencies of tests for each measurement items are varied for every facility. Therefore, a throughput of a sample analyzer indicated in a catalogue and a throughput of a sample analyzer when operated in the facility may be different. It is thus difficult to know the accurate throughput of a sample analyzer according to the actual usage situation.

SUMMARY OF THE PRESENT INVENTION

A first aspect of the present invention is an apparatus for generating throughput information of a sample analyzer capable of measuring a sample on a plurality of measurement items in which measurement time differs from each other; the apparatus comprising: a controller including a processor and a memory under control of the processor, the memory storing instructions enabling the processor to carry out operations comprising: receiving an input of a plurality of measurement orders, wherein a measurement order includes a designation of at least one measurement item; generating throughput information of the sample analyzer based on the received plurality of measurement orders; and outputting the generated throughput information.

A second aspect of the present invention is a sample analyzer for measuring a sample on a plurality of measurement items in which measurement time differs from each other; the apparatus comprising: a receiving unit for receiving an input of a plurality of measurement orders, wherein a measurement order includes a designation of at least one measurement item; a generating unit for generating throughput information of the sample analyzer based on the plurality of measurement orders received by the input unit; and an output unit for outputting the generated throughput information.

A third aspect of the present invention is a method of generating throughput information of a sample analyzer for measuring a sample on a plurality of measurement items in which measurement time differs from each other; the method comprising the steps of: receiving an input of a plurality of measurement orders, wherein a measurement order includes a designation of at least one measurement item; generating throughput information of the sample analyzer based on the received plurality of measurement orders; and outputting the generated throughput information.

A fourth aspect of the present invention is a computer program product for causing a computer including an input unit and an output unit to generate throughput information of a sample analyzer for measuring a sample on a plurality of measurement items in which measurement time differs from each other; the computer program product comprising: a computer readable medium for storing instructions enabling the computer to carry out operations comprising: receiving an input of a plurality of measurement orders, wherein a measurement order includes a designation of at least one measurement item; generating throughput information of the sample analyzer based on the received plurality of measurement orders; and outputting the generated throughput information.

BRIEF DESCRIPTION OF THE DRAWINGS

FIG. 21 is a schematic view showing one example of the content of a measurement order file;

DETAILED DESCRIPTION OF THE PREFERRED EMBODIMENTS

The preferred embodiment of the present invention will now be described with reference to the drawings.

First Embodiment

[Configuration of Sample Analyzer]

Figure 1:
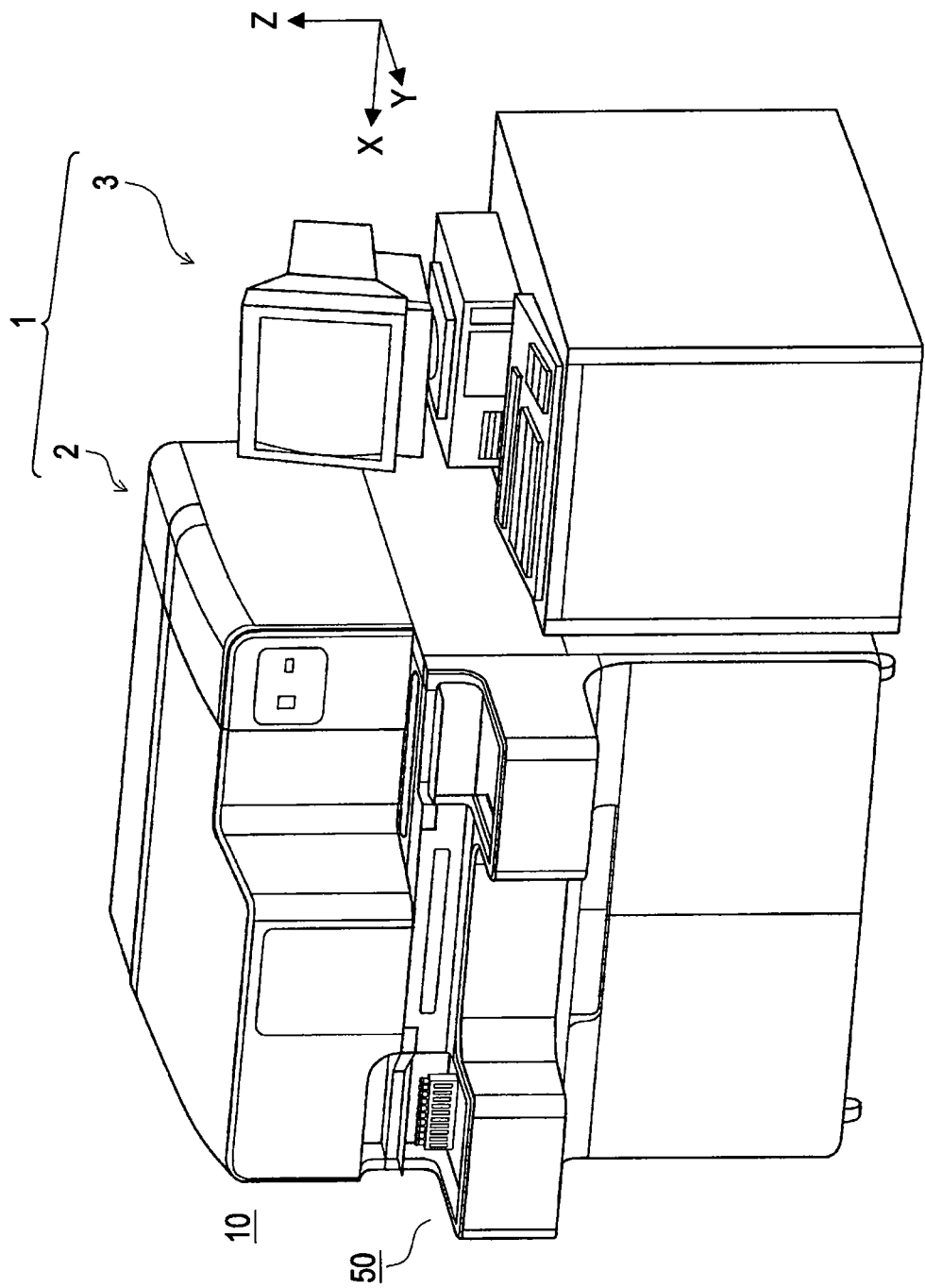
FIG. 1 is a perspective view showing a configuration of a sample analyzer according to a first embodiment.

FIG. 1 is a perspective view showing a configuration of a sample analyzer 1 according to the present embodiment. A sample analyzer 1 is configured by a measurement device 2 for optically measuring the component contained in a sample (blood), and an information processing device 3 for processing measurement data by the measurement device 2 to obtain an analysis result of the sample, and giving an operation instruction to the measurement device 2.

Figure 2:
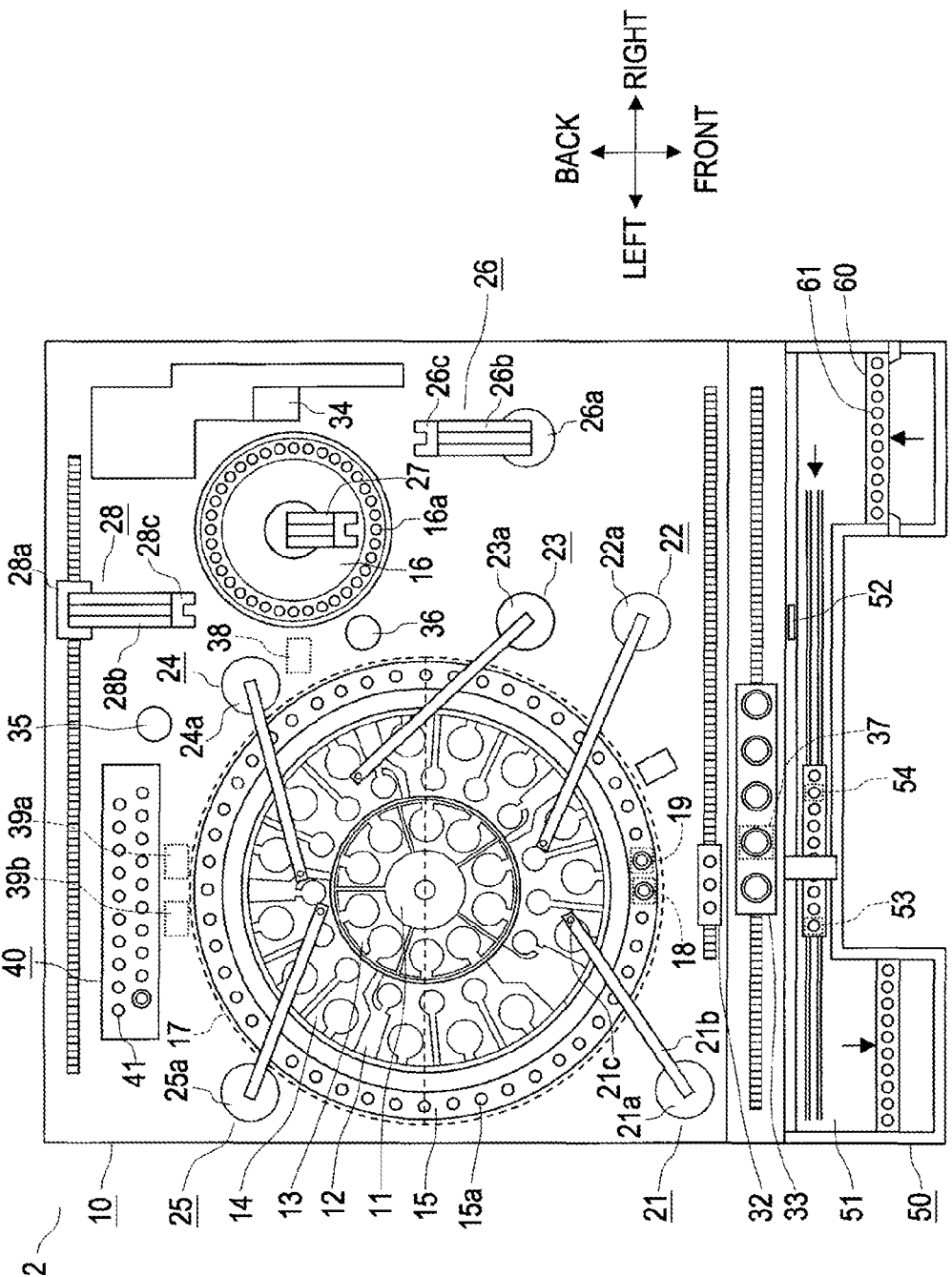
FIG. 2 is a plan view showing a schematic configuration of a measurement device included in the sample analyzer according to the first embodiment.

FIG. 2 is a plan view showing a schematic configuration of the measurement device 2. The measurement device 2 is configured by a measurement unit 10, a detection unit 40, and a transport unit 50.

The measurement unit 10 includes a first reagent table 11, a second reagent table 12, a first container rack 13, a second container rack 14, a cuvette table 15, a warming table 16, a table cover 17, a first sample dispensing unit 21, a second sample dispensing unit 22, a first reagent dispensing unit 23, a second reagent dispensing unit 24, a third reagent dispensing unit 25, a first catcher unit 26, a second catcher unit 27, a third catcher unit 28, a cuvette transport unit 32, a diluted solution transport unit 33, a cuvette port 34, and discarding ports 35, 36.

The first reagent table 11, the second reagent table 12, the cuvette table 15, and the warming table 16 are each circular tables, and are independently rotatably driven in both directions, the clockwise direction and the counterclockwise direction. The rotational drives of such tables are carried out by a plurality of stepping motors (not shown) arranged on the back side of the lower surface, respectively.

As shown in the figure, five first container racks 13 and five second container racks 14 are removably arranged on the upper surfaces of the first reagent table 11 and the second reagent table 12. The first container rack 13 and the second container rack 14 are formed with a holder for holding a reagent container.

The information on the type and the holding position of each reagent held at the first reagent table 11 and the second reagent table 12 are stored in a hard disc 304 arranged in a control unit 300 of the measurement device 2, to be described later. Thus, when the measurement of the sample is carried out, at which holding position the reagent to be used for the measurement of the sample is arranged can be specified.

As shown in the figure, the cuvette table 15 and the warming table 16 are respectively formed with a plurality of cuvette holding holes 15a, 16a along the circumference. When the cuvettes are set in the cuvette holding hole 15a, 16a, the relevant cuvettes move the circumference position in accordance with the rotation of the cuvette table 15 and the warming table 16, respectively. The warming table 16 warms the cuvette set in the holding hole 16a at a predetermined temperature.

A table cover 17 is arranged to cover the upper surfaces of the first reagent table 11, the second reagent table 12, and the cuvette table 15. Such table cover 17 can be opened when changing the reagent. The table cover 17 includes a plurality of holes (not shown). The first sample dispensing unit 21, the second sample dispensing unit 22, the first reagent dispensing unit 23, the second reagent dispensing unit 24, and the third reagent dispensing unit 25 dispense the reagent through the plurality of holes.

As shown in the figure, the first sample dispensing unit 21 includes a supporting portion 21a, an arm 21b, and a dispensing portion 21c. The supporting portion 21a is rotatably driven by a stepping motor (not shown) arranged on the back side at the lower surface. The supporting portion 21a supports the arm 21b, which arm 21b is driven in the up and down direction by the stepping motor. The dispensing portion 21c is attached at the distal end of the arm 21b and includes a pipette. The sample is aspirated and discharged using such pipette.

When the supporting portion 21a is rotatably driven, the dispensing portion 21c moves on the circumference with the supporting portion 21a as the center. The dispensing portion 21c aspirates the sample at the position immediately below at the sample aspirating position, and discharges the sample to the cuvette at the position immediately below at the sample discharging position. The second sample dispensing unit 22, the first reagent dispensing unit 23, the second reagent dispensing unit 24, and the third reagent dispensing unit 25 have configurations similar to the first sample dispensing unit 21. In other words, the second sample dispensing unit 22 includes a supporting portion 22a, which supporting portion 22a is rotatably driven by a stepping motor (not shown) arranged on the back side of the lower surface. The first reagent dispensing unit 23, the second reagent dispensing unit 24, and the third reagent dispensing unit 25 respectively includes a supporting portion 23a, a supporting portion 24a, and a supporting portion 25a, which supporting portion 23a, supporting portion 24a, and supporting portion 25a are respectively rotatably driven by a plurality of stepping motors (not shown) arranged at the back side of the lower surface.

The first catcher unit 26 is configured by a supporting portion 26a for supporting an arm 26b, the stretchable arm 26b, and a grip portion 26c. The supporting portion 26a is rotatably driven by a stepping motor (not shown) arranged on the back side at the lower surface. The grip portion 26c is attached at the distal end of the arm 26b, and can grip the cuvette. The second catcher unit 27 has a configuration similar to the first catcher unit 26, and is rotated by a stepping motor (not shown).

As shown in the figure, the third catcher unit 28 is configured by a supporting portion 28a for supporting an arm 28b, the stretchable arm 28b, and a grip portion 28c attached to a tip end of the arm 28b. The supporting portion 28a is driven along a rail arranged in a left and right direction. The supporting portion 28c can grip a cuvette.

The cuvette transport unit 32 and the diluted solution transport unit 33 are driven in the left and right direction on the rail. The cuvette transport unit 32 and the diluted solution transport unit 33 each has a hole for holding the cuvette and the diluted solution container, respectively.

A new cuvette is constantly supplied to a cuvette port 34. The new cuvette is set in the hole for holding the cuvette of the cuvette transport unit 32 and the cuvette holding hole 15a of the cuvette table 15 by the first catcher unit 26 and the second catcher unit 27. The discarding ports 35, 36 are holes for discarding the cuvette which analysis is finished which is not longer necessary The detection unit 40 includes 20 holding holes 41 for accommodating the cuvette at the upper surface, and a detecting portion (not shown) on the back side of the lower surface. When the cuvette is set in the holding hole 41, the optical information is detected from the measurement specimen in the cuvette by the detecting portion.

The transport unit 50 includes a transport path 51. The bottom surface of the transport path 51 includes a pre-analysis rack holding region on the right side, a transport region at the middle, and a post-analysis rack holding region on the left side, and is formed to a horseshoe shape. The sample barcode reader 52 reads the barcode of the barcode label attached to the sample container 61 accommodated in the sample rack 60 transported through the transport region.

Figure 3:
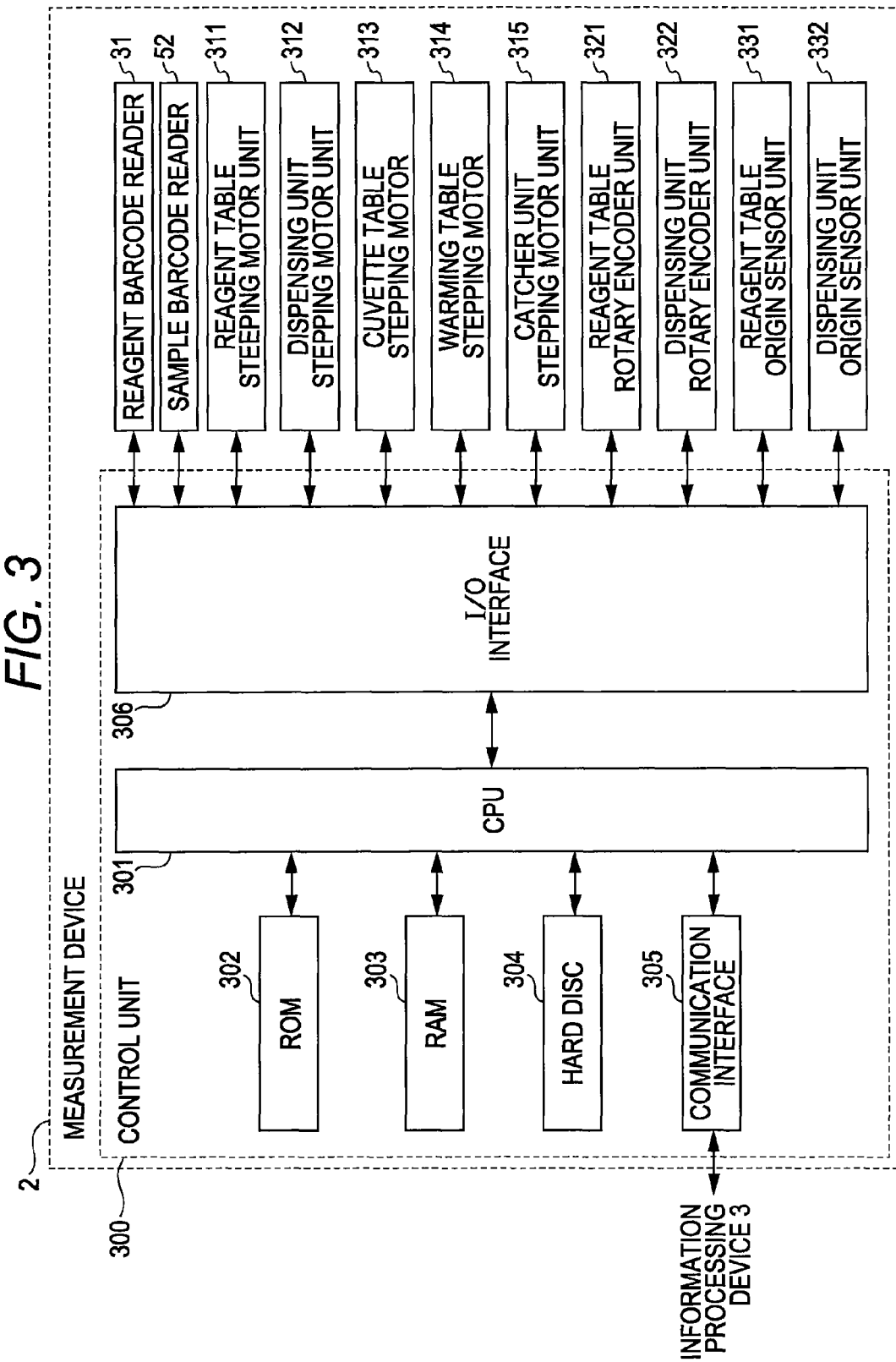
FIG. 3 is a block diagram showing a circuit configuration of the measurement device.

FIG. 3 is a block diagram showing a circuit configuration of the measurement device 2.

The measurement device 2 includes a control unit 300, a reagent barcode reader 31, a sample barcode reader 52, a reagent table stepping motor unit 311, a dispensing unit stepping motor unit 312, a cuvette table stepping motor 313, a warming table stepping motor 314, a catcher unit stepping motor unit 315, a reagent table rotary encoder unit 321, a dispensing unit rotary encoder unit 322, a reagent table origin sensor unit 331, and a dispensing unit origin sensor unit 332. The control unit 300 includes a CPU 301, a ROM 302, a RAM 303, a hard disc 304, a communication interface 305, and an I/O interface 306.

The CPU 301 executes a computer program stored in the ROM 302 and a computer program loaded in the RAM 303. The RAM 303 is used to read out the computer programs recorded on the ROM 302 and the hard disc 304. The RAM 303 is also used as a work region of the CPU 301 when executing the computer programs. The hard disc 304 is installed with various computer programs to be executed by the CPU 301 such as operating system and application program, as well as data used in executing the computer program.

That is, the control program for causing the CPU 301 to control each unit of the measurement device 2 is installed in the hard disc 404. The communication interface 305 enables transmission and reception of data with respect to the information processing device 3.

The CPU controls 301 the sample barcode reader 52, the reagent table stepping motor unit 311, the dispensing unit stepping motor unit 312, the reagent table rotary encoder unit 321, the dispensing unit rotary encoder unit 322, the reagent table origin sensor unit 331, and the dispensing unit origin sensor unit 332 through the I/O interface.

The reagent table stepping motor unit 311 includes a stepping motor for rotatably driving the first reagent table 11, and a stepping motor for rotatably driving the second reagent table 12 independent from the first reagent table 11. The dispensing unit stepping motor unit 312 includes a plurality of stepping motors for independently rotatably driving the supporting portion 21a of the first sample dispensing unit 21, the supporting portion 22a of the second sample dispensing unit 22, the supporting portion 23a of the first reagent dispensing unit 23, the supporting portion 24a of the second reagent dispensing unit 24, and the supporting portion 25a of the third reagent dispensing unit 25. The catcher unit stepping motor unit 315 includes a stepping motor for rotatably driving the supporting portion 26a of the first catcher unit 26, and a stepping motor for rotatably driving the second catcher unit 27.

The reagent table rotary encoder unit 321 includes a rotary encoder arranged in the stepping motor of the first reagent table 11, and a rotary encoder arranged in the stepping motor of the second reagent table 12. The dispensing unit rotary encoder unit 322 includes a plurality of rotary encoders arranged in the respective stepping motor of the first sample dispensing unit 21, the second sample dispensing unit 22, the first reagent dispensing unit 23, the second reagent dispensing unit 24, and the third reagent dispensing unit 25. The rotary encoder of incremental type is used herein. The rotary encoder is configured to output a pulse signal corresponding to a rotation displacement amount of the stepping motor, where the rotation amount of the stepping motor can be detected by counting the number of pulses output from the rotary encoder.

The reagent table origin sensor unit 331 includes an origin sensor for detecting that the respective rotation position of the stepping motor of the first reagent table 11 and the stepping motor of the second reagent table 12 is at the origin position. The dispensing unit origin sensor unit 332 includes an origin sensor for detecting that the respective rotation positions of the stepping motors of the first sample dispensing unit 21, the second sample dispensing unit 22, the first reagent dispensing unit 23, the second reagent dispensing unit 24, and the third reagent dispensing unit 25 are in the origin position.

Figure 4:
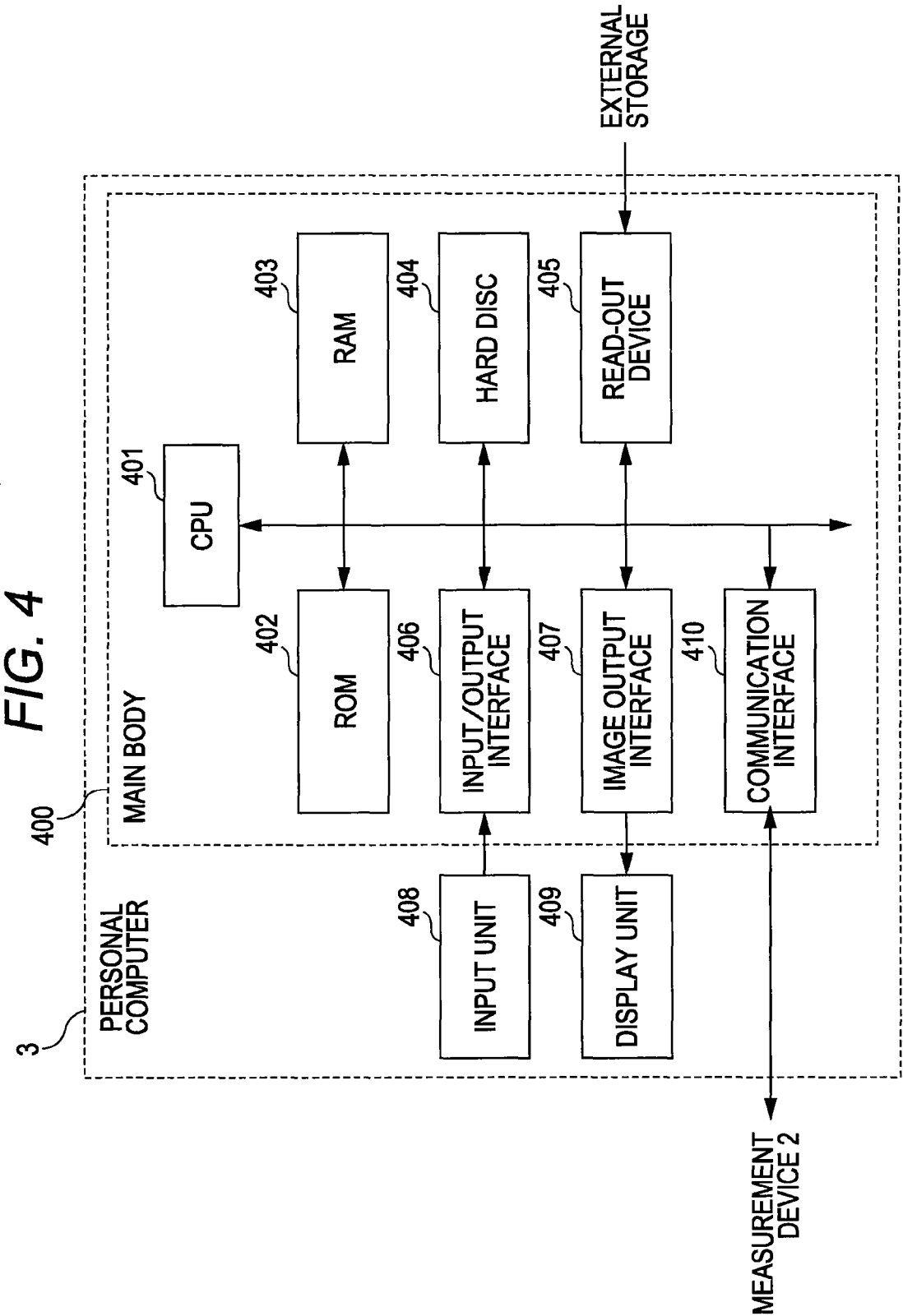
FIG. 4 is a block diagram showing a configuration of an information processing device of the sample analyzer according to the first embodiment.

FIG. 4 is a block diagram showing a configuration of the information processing device 3.

The information processing device 3 includes a personal computer configured by a main body 400, an input unit 408, and a display unit 409. The main body 400 includes a CPU 401, a ROM 402, a RAM 403, a hard disc 404, a read-out device 405, an input/output interface 406, an image output interface 407, and a communication interface 410.

The CPU 401 executes a computer program stored in the ROM 402 and a computer program loaded in the RAM 403. The RAM 403 is used to read out the computer programs recorded on the ROM 402 and the hard disc 404. The RAM 403 is also used as a work region of the CPU 401 when executing the computer programs.

The hard disc 404 is installed with various computer programs to be executed by the CPU 401 such as operating system and application program, as well as data used in executing the computer program. That is, the computer program for causing the computer to function as the information processing device according to the present embodiment is installed in the hard disc 404.

The read-out device 405 is configured by CD drive, DVD drive, and the like, and is able to read out computer programs and data recorded on a recording medium. The input unit 408 including keyboard and mouse is connected to the input/output interface 406, so that the user can use the input unit 408 to input data to the information processing device 3. The image output interface 407 is connected to the display unit 409 configured by CRT, liquid crystal panel, or the like, and outputs an image signal corresponding to the image data to the display unit 409. The display unit 409 displays the image based on the input image signal. The information processing device 3 enables transmission and reception of data with respect to the measurement device 2 by the communication interface 410.

[Operation of Sample Analyzer]

The operation of the sample analyzer 1 according to the present embodiment will be described below.

<Analyzing Procedure for Every Sample>

First, the procedure of analyzing the sample will be described. The analyzing procedure of the sample differs depending on the measurement item (PT, APTT, etc.) of the sample. The measurement item of the sample is specified by the measurement order. In the sample analyzer 1, the measurement order can be registered by the user, and the measurement order can be received from a server device (not shown). That is, when the user registers the measurement order, the user operates the input unit 408 of the information processing device 3 to input the measurement order to the sample analyzer 1. When receiving the measurement order from the server device, the user registers the measurement order in the server device in advance. In the present embodiment, the measurement order refers to specifying one or a plurality of measurement items with respect to the individual sample and commanding the sample analyzer 1 of the measurement of the specified measurement items. Therefore, one measurement order is input with respect to one sample, and one or a plurality of measurement items is contained in one measurement order.

The sample rack 60 accommodating a plurality of sample containers 61 is set in the pre-analysis rack holding region of the transport path 51 by the user. The sample rack 60 is moved to the back side in the pre-analysis rack holding region, and then moved towards the left in the transport region. In this case, the barcode label attached to the sample container 61 is read by the sample barcode reader 52. The sample ID is recorded in the barcode of the sample container 61, so that the information processing device 3 acquires the measurement order of the relevant sample with the read sample ID as the key. That is, the measurement order corresponding to the sample ID is read from the hard disc 404 of the information processing device 3 when the measurement order is registered in the sample analyzer 1 by the user, and the sample ID is transmitted from the information processing device 3 to the server device, and the server device transmits the measurement order corresponding to the received sample ID to the information processing device 3 and the information processing device 3 receives the measurement order when acquiring the measurement order from the server device.

Thereafter, the sample rack 60 is positioned at a predetermined location of the transport region. After the aspiration of the sample is terminated in the transport region, the sample rack 60 is moved towards the left in the transport region, and then moved to the front side in the post-analysis rack holding region.

Primary Dispensing of Sample

The second catcher unit 27 sets the cuvette supplied to the cuvette port 34 to the cuvette holding hole 15a of the cuvette table 15. The first sample dispensing unit 21 aspirates the sample of the sample container 61 positioned at a predetermined sample aspirating position 53 of the transport region of the transport path 51. The sample aspirated by the first sample dispensing unit 21 is discharged to the cuvette set in the cuvette holding hole 15a positioned at the sample discharging position 18 at the front position of the cuvette table 15. After discharging the sample, the dispensing portion 21c of the first sample dispensing unit 21 is cleaned.

Secondary Dispensing of Sample

The first catcher unit 26 sets the cuvette supplied to the cuvette port 34 to the cuvette holding hole of the cuvette transport unit 32. The second sample dispensing unit 22 aspirates the sample accommodated in the cuvette at the sample aspirating position 19 or the sample of the sample container 61 positioned at a predetermined sample aspirating position 54 of the transport region of the transport path 51. The sample aspirated by the second sample dispensing unit 22 is discharged to the cuvette set in the cuvette transport unit 32. The second sample dispensing unit 22 can aspirate the diluted solution set in the diluted solution transport unit 33. In this case, the second sample dispensing unit 22 aspirates the diluted solution at a diluted solution aspirating position 37 before the aspiration of the sample, and then aspirates the sample at the sample aspirating position 19 or 54.

If a measurement order including a plurality of measurement items is acquired for one sample, the sample is divided into the cuvette for the number of measurement items from the cuvette set in the cuvette holding hole 15a of the cuvette table 15 (secondary dispensing). Each cuvette corresponds to the measurement item one by one, and the sample divided to the cuvette is measured for the measurement item corresponding to the cuvette.

The cuvette transport unit 32 is driven on the rail towards the right at a predetermined timing when the sample is discharged (secondary dispensing) to the accommodated cuvette. Thereafter, the cuvette accommodating the sample set in the cuvette transport unit 32 is gripped and set in the cuvette holding hole 16a of the warming table 16 by the first catcher unit 26.

When the cuvette held in the cuvette holding hole 15a of the cuvette table 15 is no longer necessary after the sample is aspirated, the cuvette table 15 is rotated and positioned at a place close to the second catcher unit 27. The second catcher unit 27 grips the cuvette, which became unnecessary, held in the cuvette holding hole 15a, and discards the same to the discarding port 36.

Warming of Sample

The sample accommodated in the cuvette is time warmed according to the measurement item in the warming table 16. For instance, the sample is warmed for three minutes when the measurement item is PT, and the sample is warmed for one minute when the measurement item is APTT.

After the sample is warmed, a trigger reagent is mixed to the sample. Depending on the measurement item, an intermediate reagent is dispensed to the cuvette after the sample is warmed for a predetermined time, and the trigger reagent is dispensed after the cuvette is warmed for a predetermined time again. For instance, when the measurement item is PT, the PT reagent (trigger reagent) is dispensed to the cuvette accommodating the warmed sample, and thereafter, the optical measurement is carried out in the detection unit 40.

In this case, the cuvette held in the cuvette holding hole 16a of the warming table 16 is gripped by the third catcher unit 28, and positioned at a reagent discharging position 39a or 39b. The trigger reagent in a predetermined reagent container (not shown) arranged in the first reagent table 11 or the second reagent table 12 is aspirated by the second reagent dispensing unit 24 or the third reagent dispensing unit 25, and the trigger reagent is discharged at the reagent discharging position 39a or 39b.

A case in which the intermediate reagent is mixed to the warmed sample, and then again warmed will now be described. For instance, when the measurement item is APTT, the APTT reagent (intermediate reagent) is dispensed to the cuvette accommodating the warmed sample, and thereafter, again warmed in the warming table 16 for two minutes. Subsequently, calcium chloride solution (trigger reagent) is dispensed into the cuvette, and optical measurement is carried out in the detection unit 40. Therefore, in the case of the measurement item in which the sample is warmed two times, the sample is warmed for a predetermined time in the warming table 16, and then the second catcher unit 27 grips the cuvette accommodating the sample set in the holding hole 16a and moves the same to the reagent discharging position 38. The first reagent dispensing unit 23 aspirates the intermediate reagent in the predetermined reagent container (not shown) arranged in the first reagent table 11 or the second reagent table 12, and discharges the intermediate reagent at the reagent discharging position 38. Thus, after the intermediate reagent is discharged, the second catcher unit 27 stirs the relevant cuvette, and again sets such cuvette in the cuvette holding hole 16a of the warming table.

The cuvette held in the cuvette holding hole 16a of the warming table 16 is gripped by the third catcher unit 28, and positioned at the reagent discharging position 39a or 39b. The second reagent dispensing unit 24 or the third reagent dispensing unit 25 aspirates the trigger reagent in a predetermined reagent container (not shown) arranged in the first reagent table 11 or the second reagent table 12 and discharges the trigger reagent at the reagent discharging position 39a or 39b.

Light Measurement

After the trigger reagent is discharged in such manner, the third catcher unit 28 sets the cuvette, to which the reagent is discharged, in the holding hole 41 of the detection unit 40. The optical information is then detected from the measurement specimen accommodated in the cuvette in the detection unit 40.

The cuvette, which optical measurement by the detection unit 40 is finished and which is no longer necessary, is moved to immediately above the discarding port 35 while being gripped by the third catcher unit 28, and discarded to the discarding portion 35.

Measurement Data Analysis

The optical information detected by the detection unit 40 is transmitted to the information processing device 3. The CPU 401 of the information processing device 3 processes the acquired optical information to obtain the analysis result of the sample. The analysis result obtained in such manner is stored in the hard disc 404 in correspondence with the sample information such as the sample ID, and output to the display unit 409.

<Throughput Estimating Operation>

The sample analyzer 1 according to the first embodiment can execute a throughput estimating operation of estimating the throughput of the sample analyzer 1. The throughput estimating operation is realized by having the CPU 401 of the information processing device 3 execute the sample throughput estimating process to be described below.

Figure 5:
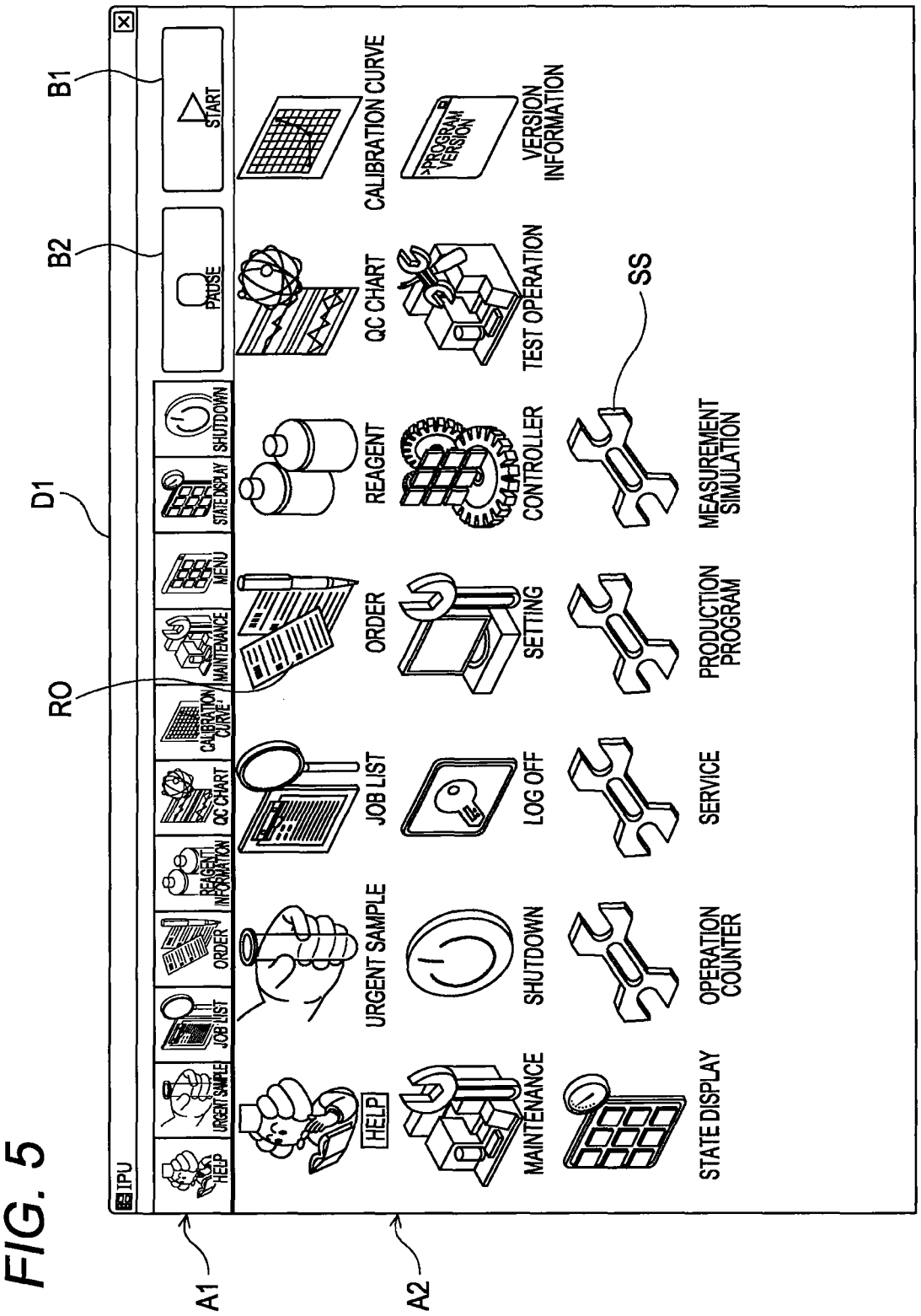
FIG. 5 is a view showing a menu screen of the sample analyzer according to the first embodiment.

The sample analyzer 1 is used by a plurality of users. The user includes an operator who operates the sample analyzer 1 to inspect the sample, a manager who manages the sample analyzer 1, a service man of a manufacturing company who carries out maintenance of the sample analyzer 1, and the like. Therefore, the user information is stored and the user ID, the password, the authorization, and the like of each user are registered in the hard disc 404 of the information processing device 3. When using the sample analyzer 1, the user starts up the sample analyzer 1, operates the input unit 408 of the information processing device, and inputs a user ID and a password to try logging into the information processing device 3. If the user login to the sample analyzer 1 is successful, a menu screen is displayed on the display unit 409. FIG. 5 is a view showing a menu screen. The menu screen D1 includes a tool bar A1 in which a plurality of buttons are lined in a row, and a work region A2 arranged on the lower side of the tool bar A1. The display screen of the information processing device 3 is provided with the tool bar A1 and the work region A2 common, where the display content of the work region A2 differs depending on the display screen. The tool bar A1 includes buttons for calling out functions used frequently such as a start button B1 for instructing the start of sample measurement and a pause button B2 for pausing the sample measurement.

A plurality of icons is displayed in the work region A2 of the menu screen D1. Such icons include icons for calling out various functions of the sample analyzer 1 such as the measurement order input function, the shutdown function, the setting function, and the sample throughput estimating function, where each icon can be selected through the double click operation of the mouse, and the corresponding function is called out by selecting the icon. The icon RO with a character string "order" is an icon for calling out the measurement order registration process, where the measurement order registration process to be described later is started up by selecting the icon RO. The icon SS with a character string "measurement simulation" is an icon for calling out the sample throughput estimating process, where the sample throughput estimating process to be described later is started up by selecting the icon SS. The icon SS is a special icon that is displayed on the menu screen D1 only when the user having authority as a service man logs in. That is, the service man needs to log into the sample analyzer 1 in order for the sample analyzer 1 to execute the throughput estimating operation.

The "icon" referred to herein refers to an image assigned with a specific function and designed to symbolically represent such function, and include those displayed in the window.

Figure 6:
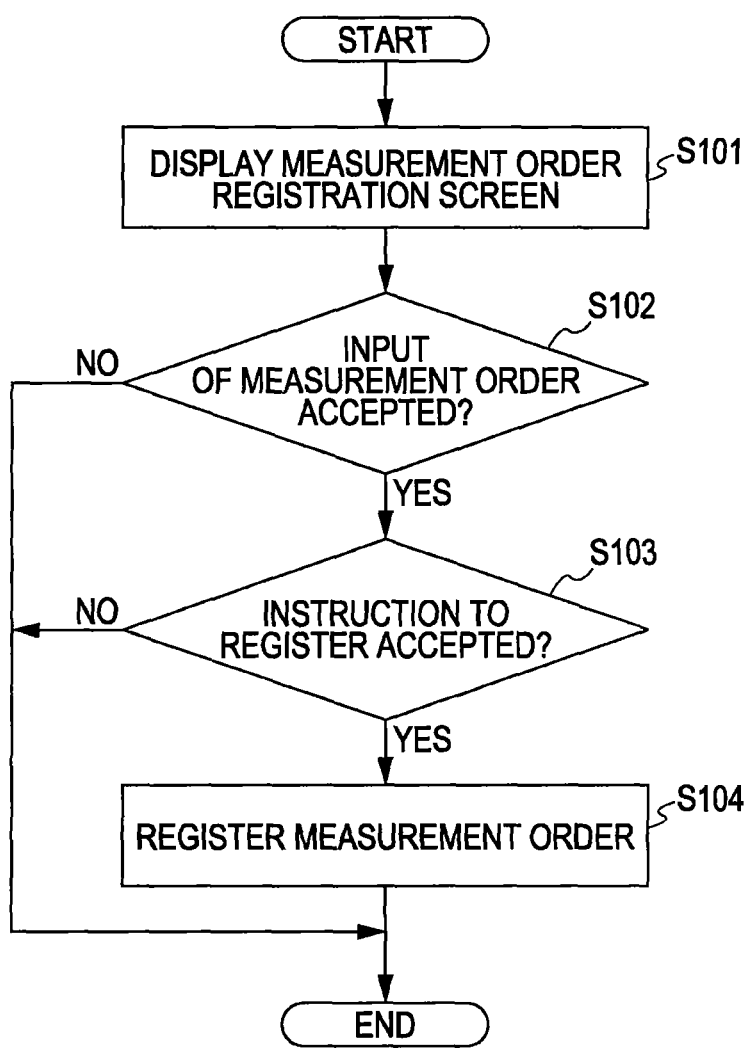
FIG. 6 is a flowchart showing a procedure of the measurement order registration process of the sample analyzer according to the first embodiment.

The user registers the measurement order in the sample analyzer 1 prior to the throughput estimating operation. FIG. 6 is a flowchart showing the procedure of the measurement order registration process. The CPU 401 receives an instruction to execute the measurement order registration process from the user with the menu screen D1 displayed. When the user operates the input unit 408 to select the icon RO and instructs the execution of the measurement order registration process to the information processing device 3, the CPU 401 starts the measurement order registration process and displays a measurement order registration screen on the display unit 409 (step S101).

Figure 7:
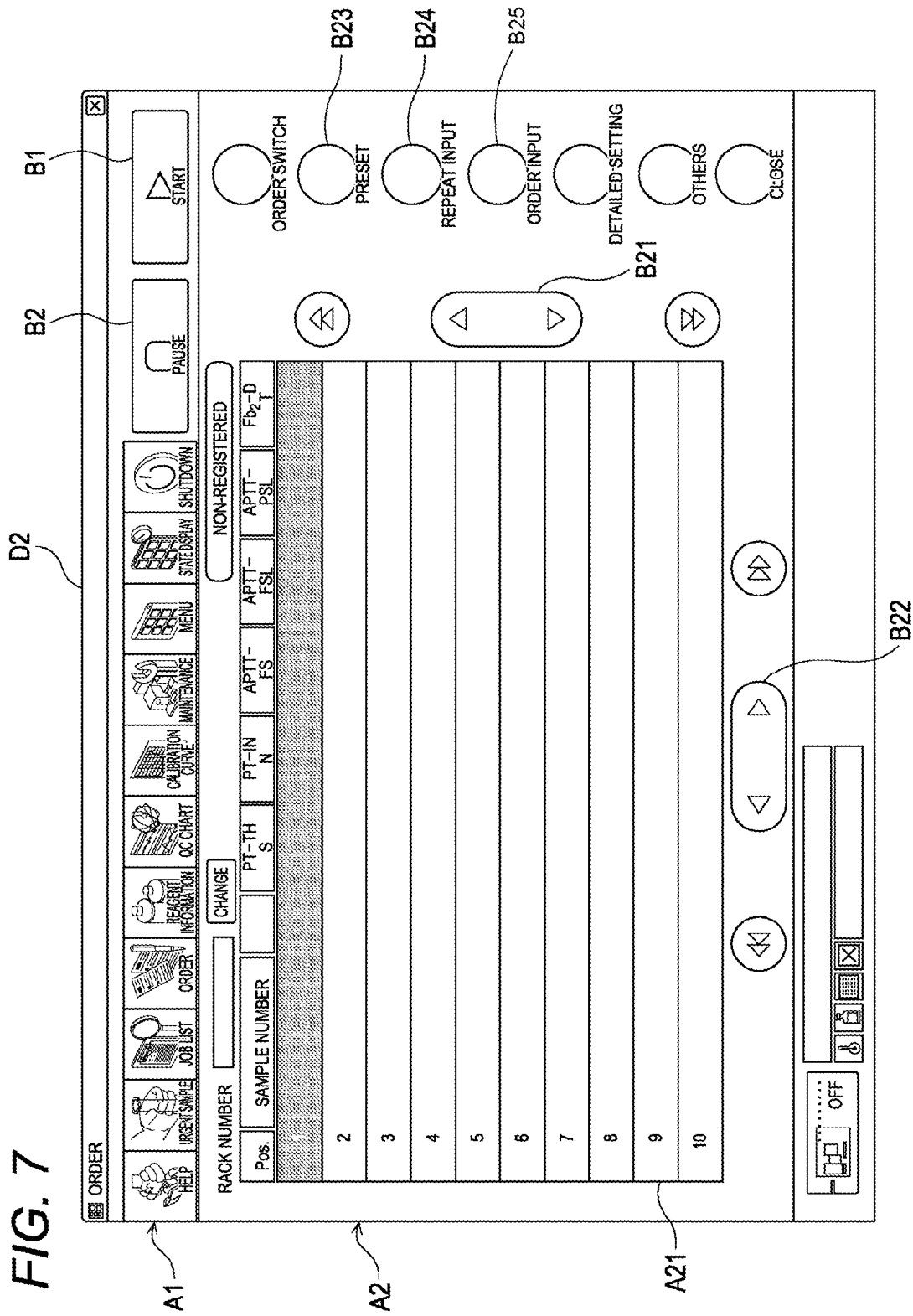
FIG. 7 is a view showing one example of a measurement order registration screen of the sample analyzer of the first embodiment.

FIG. 7 is a view showing one example of the measurement order registration screen. In FIG. 7, a state in which the measurement order is not input is shown. The work region A2 of the measurement order registration screen D2 includes a list region A21 for displaying ten measurement orders, which is the same number as the sample container held in one sample rack. In such list region A21, the order information on the holding position, the sample number, and each measurement item in the sample rack is displayed for every row. The order information is information indicating the instruction to execute the sample measurement for the corresponding measurement item, and is displayed as a check symbol (see FIG. 8). The measurement order input in the throughput estimating operation is a virtual measurement order, different from the measurement order for actually commanding the analysis of the actual sample to the sample analyzer. Therefore, even if the measurement order is input in the throughput estimating operation, the analysis by the sample analyzer is not executed based on the input measurement order.

The work region A2 of the measurement order registration screen D2 includes a rack number input region for inputting a rack number of a sample rack, and scroll buttons B21 and B22 for scrolling the display of the list region A21, a preset button B23 for inputting order information stored in advance, a repeat input button B24 for repeatedly inputting once input order information, and the like. The work region A2 of the measurement order registration screen D2 also includes a register button B25 for registering the input measurement order to the measurement order database arranged in the hard disc 404. The buttons B21 to B25 are selection graphical user interface objects (control) that can be selected by the click operation of the mouse, where the assigned function (scroll function, register function of measurement order, etc.) is executed when selected.

Figure 8:
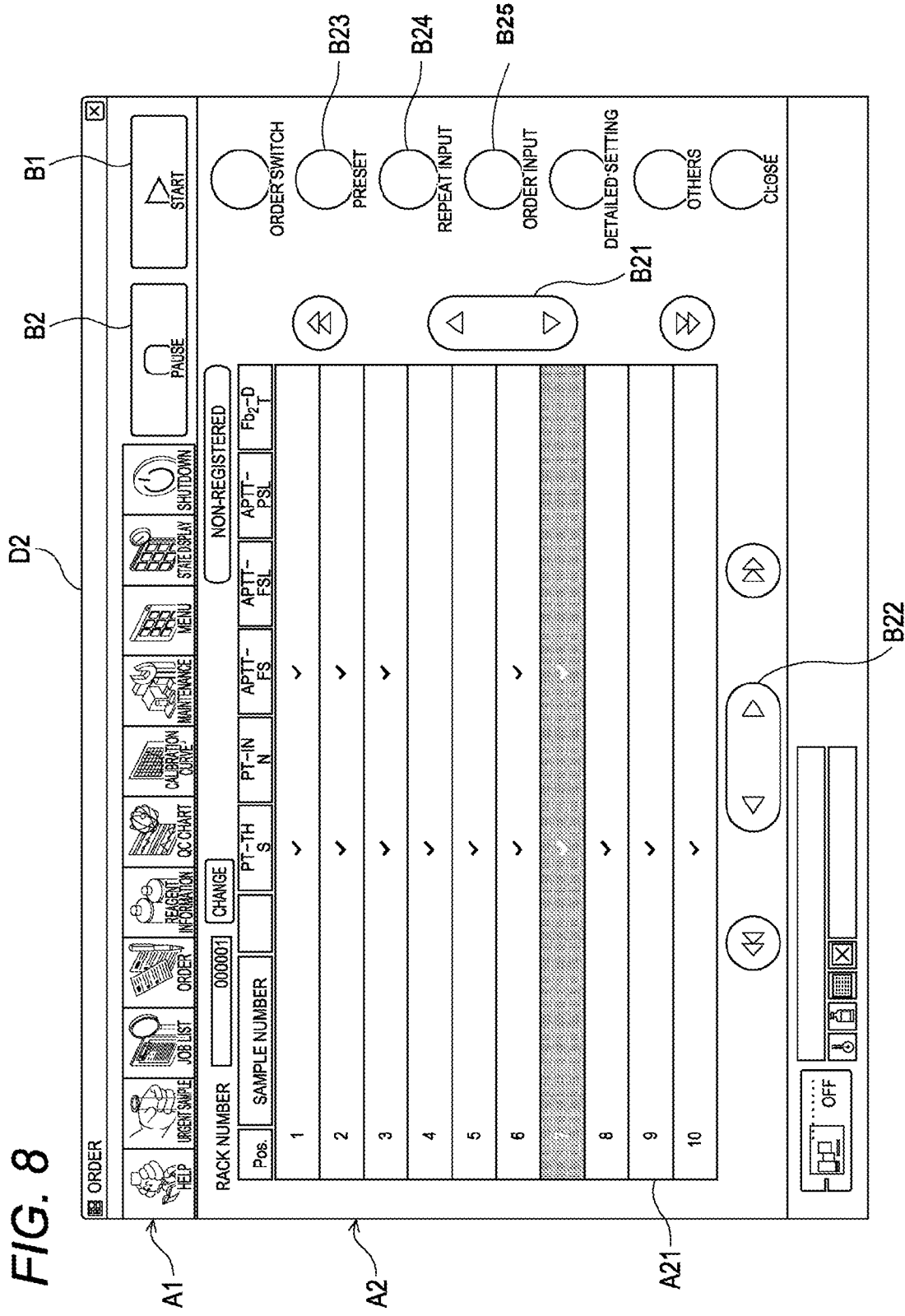
FIG. 8 is a view showing another example of a measurement order registration screen of the sample analyzer of the first embodiment.

The user inputs the measurement order to the information processing device 3 in the measurement order registration screen D2. FIG. 8 is a view showing another example of the measurement order registration screen. FIG. 8 shows a screen example after the measurement order is input. The user inputs the rack number to the rack number input region, and inputs the sample number and the order information to the list region A21. The preset button B23, the repeat input button B24, and the like can be used for the input of the measurement order. In the illustrated example, the order information is input to the measurement item "PT-THS" for all ten samples displayed in the list region A21, and the order information is input to the measurement item "APTT-FS" for the samples at the holding positions 1 to 3, 6, and 7. That is, the measurement instruction of "PT-THS" is given to the samples of the holding positions 1 to 10, and the measurement instruction of "APTT-FS" is given to the samples of the holding positions 1 to 3, 6 and 7.

The CPU 401 receives the input of the measurement order as described above (YES in step S102). When receiving the input of the measurement order, the CPU 401 receives the registration instruction of the measurement order when the user selects the register button B25 (YES in step S103). When receiving the registration instruction of the measurement order, the CPU 401 registers the input measurement order in the measurement order database of the hard disc 404 (step S104), and terminates the process. Furthermore, when the measurement order is not input (NO in step S102), and when the registration instruction is not given although the measurement order is input (NO in step S103), the CPU 401 terminates the process.

Figure 9:
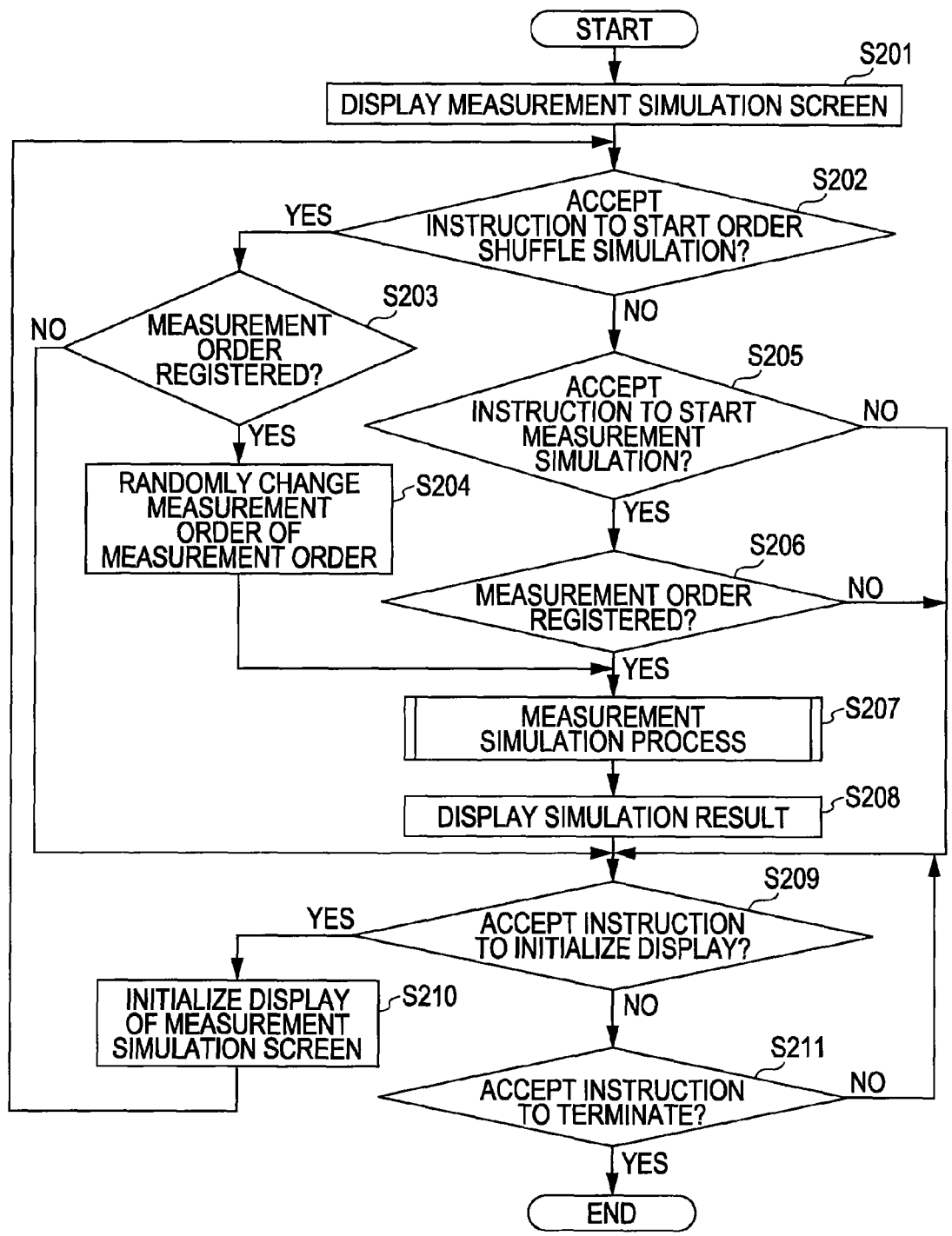
FIG. 9 is a flowchart showing the procedure of the sample throughput estimating process of the sample analyzer according to the first embodiment.

The user causes the information processing device 3 to execute the sample throughput estimating process described below when hoping to know about the throughput of the sample analyzer 1 with respect to the measurement order registered in the above manner. FIG. 9 is a flowchart showing the procedure of the sample throughput estimating process.

The CPU 401 receives the execution instruction of the sample throughput estimating process from the user with the menu screen D1 displayed. When the user operates the input unit 408 and selects the icon SS to instruct the information processing device 3 to execute the sample throughput estimating process, the CPU 401 starts the sample throughput estimating process and displays the measurement simulation screen on the display unit 409 (step S201).

Figure 10:
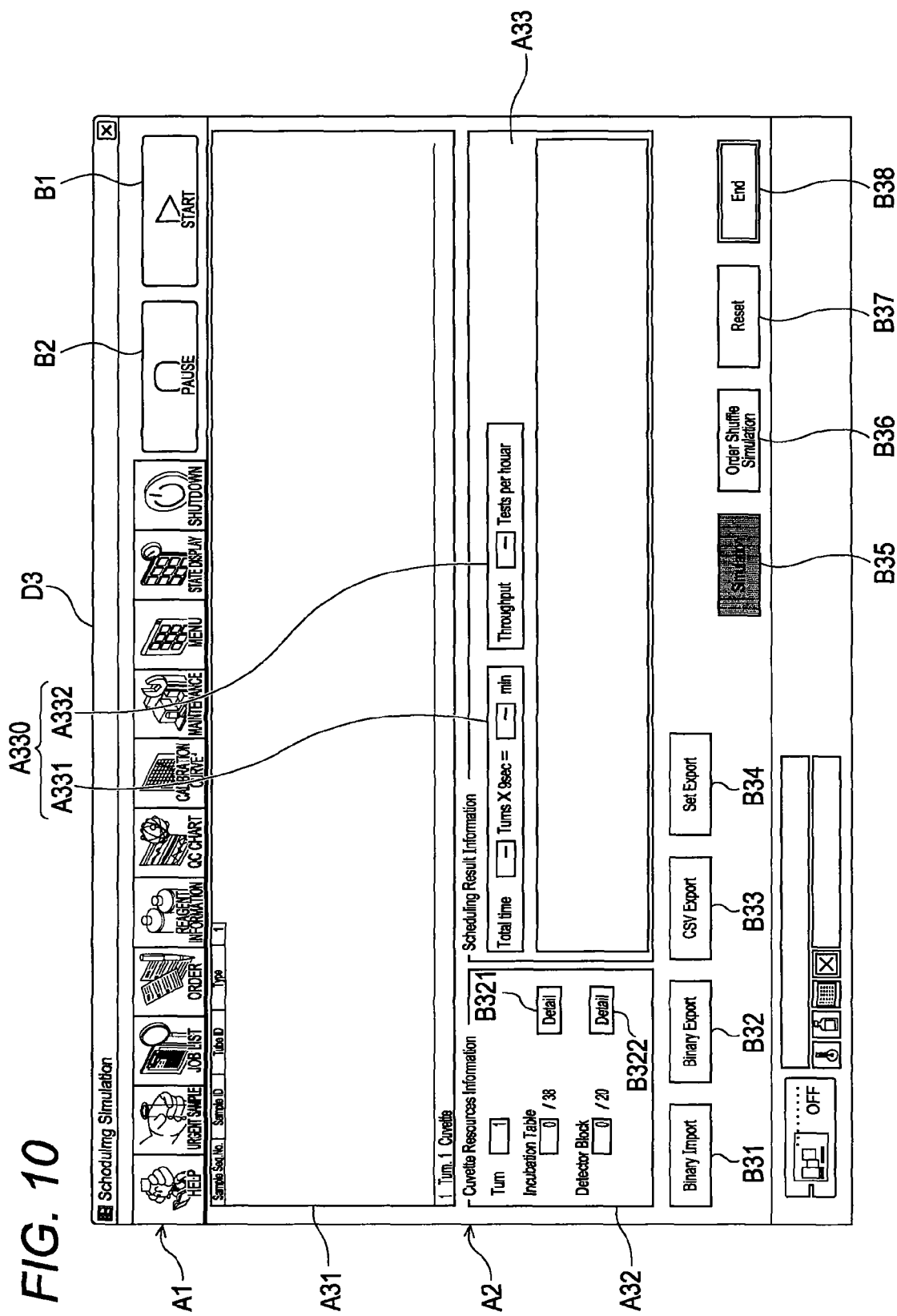
FIG. 10 is a view showing one example of a measurement simulation screen of the sample analyzer according to the first embodiment.

FIG. 10 is a view showing one example of the measurement simulation screen. In FIG. 10, the measurement simulation screen in a state the measurement simulation is not executed is shown. The work region A2 of the measurement simulation screen D3 includes a schedule table display region A31 for displaying the schedule of the sample measurement created by the measurement simulation in a timing chart form. At the lower side of the schedule table display region A31, a cuvette information display region A32 for displaying the usage status of the warming table 16 and the detection unit 40 obtained by the measurement simulation, and a schedule result display region A33 for displaying throughput information A330 including a total processing time A331 obtained by the measurement simulation and an average number of processing tests A332 per unit time are arranged. Nothing is displayed in the schedule table display region A31, the cuvette information display region A32, and the schedule result display region A33 before the measurement simulation is executed.

The buttons B31 to B38, which are selection graphical user interface objects, are arranged on the lower side of the cuvette information display region A32 and the schedule result display region A33 of the work region A2.

The button B31 is a button for reading an output file of binary form indicating the results of the past measurement simulation, and redisplaying the results of the measurement simulation. The button B32 is a button for outputting the displayed results of the measurement simulation as a file of binary form. The button B33 is a button for outputting the displayed results of the measurement simulation as a file of CSV (Comma Separated Values) form. The button B34 is a button for generating a set data including the output file of binary form and the output file of the CSV form from the displayed results of the measurement simulation and storing the set data in the new folder.

The button B35 is a button for instructing the start of the measurement simulation by the registered measurement order. The button B36 is a button for randomly changing the measurement order of each sample of the registered measurement order and instructing the start of the measurement simulation. The button B37 is a button for initializing the display of the measurement simulation screen D3 (to obtain a state in which the results of the measurement simulation are not displayed). The button B38 is a button for closing the measurement simulation screen D3.

The CPU 401 determines whether or not the selection of the button B36 is received, that is, whether or not an instruction to randomly change the measurement order of each sample of the registered measurement order and start the measurement simulation (hereinafter referred to as "order shuffle simulation") is received in the measurement simulation screen D3 (step S202). The CPU 401 determines whether or not the measurement order is registered (step S203) when receiving the instruction to start the order shuffle simulation (YES in step S202), and proceeds the process to step S209 if the measurement order is not registered (NO in step S203).

If the measurement order is registered in step S203 (YES in step S203), the CPU 401 randomly changes the measurement order of the samples of the registered measurement order (step S204), and executes the measurement simulation process (step S207).

The CPU 401 determines whether or not the selection of the button B35 is received, that is, whether or not the instruction to start the measurement simulation by the registered measurement order is received (step S205) when not receiving the instruction to start the order shuffle simulation in step S202 (NO in step S202). The CPU 401 determines whether or not the measurement order is registered (step S206) when receiving the instruction to start the simulation (YES in step S205), and proceeds the process to step S209 if the measurement order is not registered (NO in step S206). The CPU 401 proceeds the process to step S209 also when not receiving the instruction to start the measurement simulation in step S205 (NO in step S205).

If the measurement order is registered in step S206 (YES in step S206), the CPU 401 executes the measurement simulation process (step S207). If an instruction to start the measurement simulation is given in step S205, the measurement simulation is executed assuming the samples are measured in the registered order of each measurement order.

Figure 11:
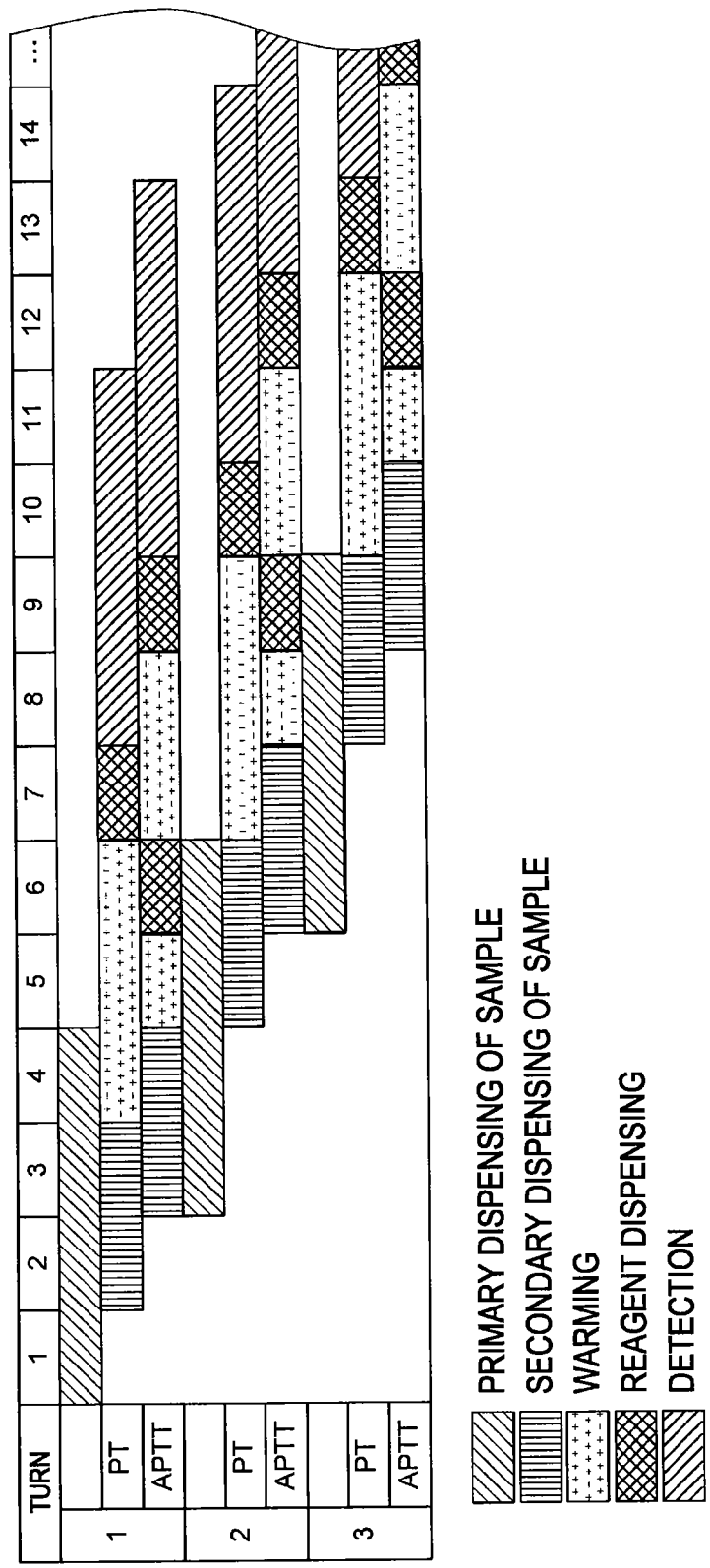
FIG. 11 is a timing chart partially showing one example of a sample measurement schedule according to the sample analyzer according to the first embodiment.

In the measurement simulation process, the sample measurement schedule that can be executed by the actual measurement device 2 is created. FIG. 11 is a timing chart partially showing one example of the sample measurement schedule. As shown in the figure, the sample measurement schedule is created by assigning the operation to be executed for every continuous turn sectionalized by a predetermined time interval (e.g. nine seconds). In the example of FIG. 11, the measurement of the measurement items PT and APTT is instructed for each sample of the sample numbers 1 to 3. For the sample of sample number 1, the primary dispensing of the sample is scheduled in the first to fourth turns, the secondary dispensing of the sample for the PT (dispensing of the sample from the cuvette held in the cuvette table 15 to the cuvette set in the cuvette transport unit 32 by the second sample dispensing unit 22) is scheduled in the second to third turns, and the secondary dispensing of the sample for the APTT is scheduled in the third to fourth turns. For the sample for the PT, the warming of the sample is scheduled in the fourth to sixth turns, the dispensing of the PT reagent to the sample is scheduled in the seventh turn, and the optical measurement is scheduled in the eighth to eleventh turns. For the sample for the APTT, the warming of the sample is scheduled in the fifth turn, the dispensing of the APTT reagent to the sample is scheduled in the sixth turn, the second warming of the sample is scheduled in the seventh and eighth turns, the dispensing of the calcium chloride solution to the sample is scheduled in the ninth turn, and the optical measurement is scheduled in the tenth to thirteenth turns. For the sample of sample number 2, schedule similar to the sample number 1 is scheduled to start after a few turns, and for the sample of sample number 3, schedule similar to the sample number 1 is scheduled to start after another few turns.

Therefore, a plurality of operations is simultaneously executed in parallel in the sample analyzer 1. For instance, the warming operation for the sample of the measurement item PT of the sample number 1, the secondary dispensing operation for the sample of the sample number 2, the secondary dispensing operation for the sample of the sample number 3, and the like are executed in parallel. In the measurement device 2, the sample operation is executed such that the same mechanism portion (e.g., first reagent dispensing unit 23) is not used in two operations in the same turn, and also such that the entire measurement operation of the sample is terminated in as few number of turns as possible. In the measurement simulation process, the sample measurement schedule same as the actual operation of the measurement device 2 is created.

Figure 12:
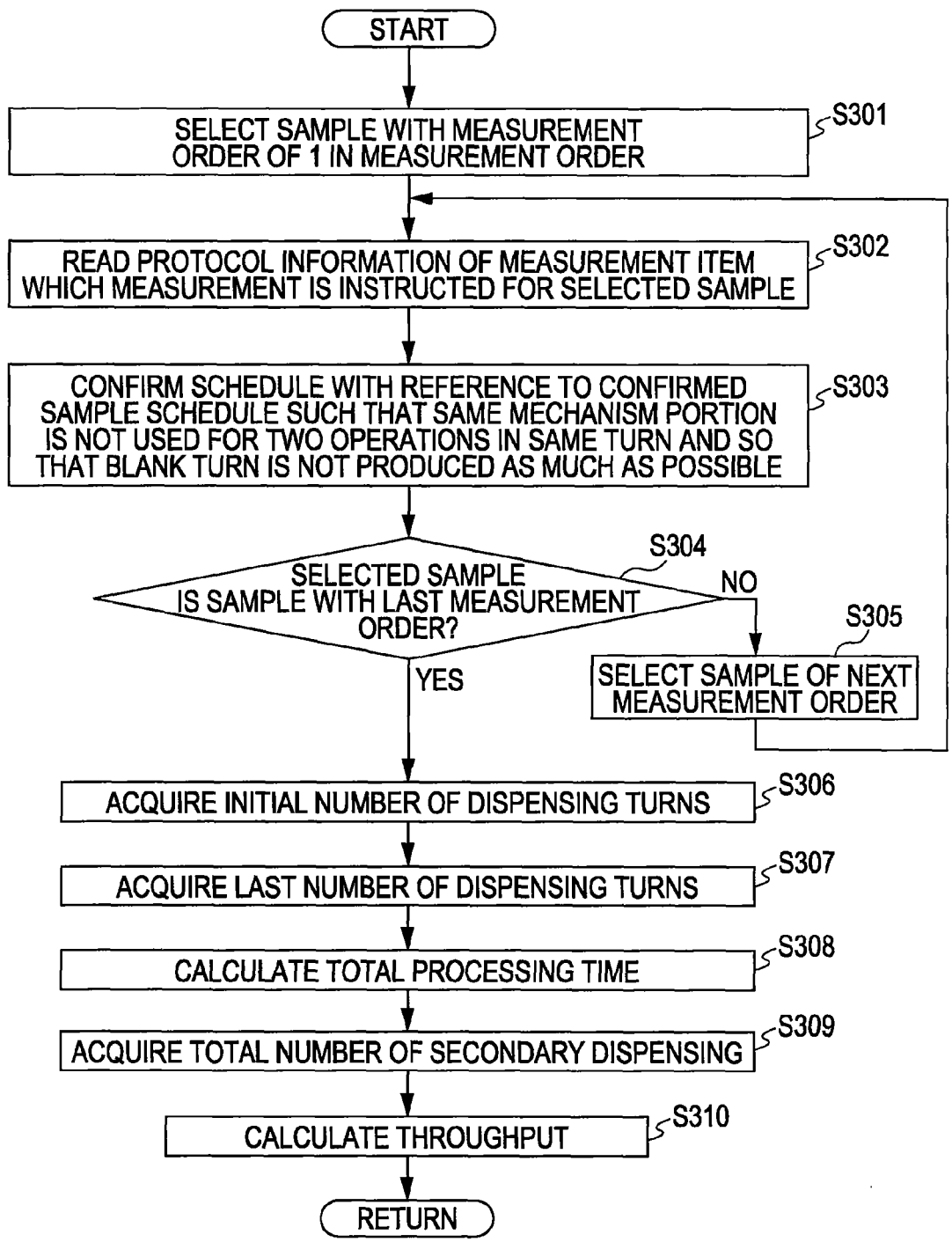
FIG. 12 is a flowchart showing a procedure of the measurement simulation process of the sample analyzer according to the first embodiment.

The measurement simulation process will be described in detail below. FIG. 12 is a flowchart showing the procedure of the measurement simulation process. In the measurement simulation process, the CPU 401 first selects the sample having the measurement order of 1 in the registered measurement order (step S301). The hard disc 404 stores information of the sample measurement protocol (amount of sample, warming time of sample, type and amount of reagent, etc.) for every measurement item, where the CPU 401 specifies the measurement item which measurement is instructed for the selected sample, and reads out the protocol information for such measurement item from the hard disc 404 (step S302). Thereafter, the CPU 401 references the schedule for the already confirmed sample, and confirms the schedule for the selected sample such that the same mechanism portion is not used in two operations in the same turn and such that a turn in which none of the mechanism portion is not used does not produce as much as possible (step S303).

The CPU 401 then determines whether or not the selected sample is the sample having the last measurement order in the measurement order (step S304). If the currently selected sample is not the sample having the last measurement order (NO in step S304), the CPU 401 selects the sample of the next measurement order (step S305), and returns the process to step S302.

If the current selected sample is the sample having the last measurement order in step S304 (YES in step S304), the CPU 401 acquires the turn number of the turn assigned with the secondary dispensing of the first sample (hereinafter referred to as "initial dispensing turn number") in the created schedule (step S306), and acquires the turn number of the turn assigned with the secondary dispensing of the last sample (hereinafter referred to as "last dispensing turn number")(step S307). The CPU 401 then calculates the total processing time, that is, the time from the start of the sample measurement until the measurement of the last sample is completed (step S308). The total processing time is derived from equation (1).

[Equation 1]

$$\text{timeSpanSec} = (\text{lastDispTurn} - \text{firstDispTurn} + 1) \times \text{turnSec} \qquad (1)$$

Here, timeSpanSec indicates the total processing time, lastDispTurn indicates the last number of calculates turns, firstDispTurn indicates the initial dispensing turn number, and turnSec indicates the time for one turn.

The CPU 401 then acquires the total number of secondary dispensing in the created sample measurement schedule (step S309), and calculates the average number of processing tests per one hour (step S310). The average number of processing tests per one hour is obtained by equation (2). The number of tests is the number of measurement items contained in all registered measurement orders, that is, the number of optical measurements by the detection unit 40. The number of tests is also referred to as number of samples divided into cuvettes by secondary dispensing.

[Equation 2]

$$\text{throughput} = \text{dispCount}/\text{timeSpanSec} \times 3600 \qquad (2)$$

There, throughput indicates the average number of processing tests per one hour, and dispCount indicates the total number of secondary dispensing in the created sample measurement schedule.

After the process of step S310 is finished, the CPU 401 returns the process to the callout address process of the measurement simulation process in the main routine.

Figure 13:
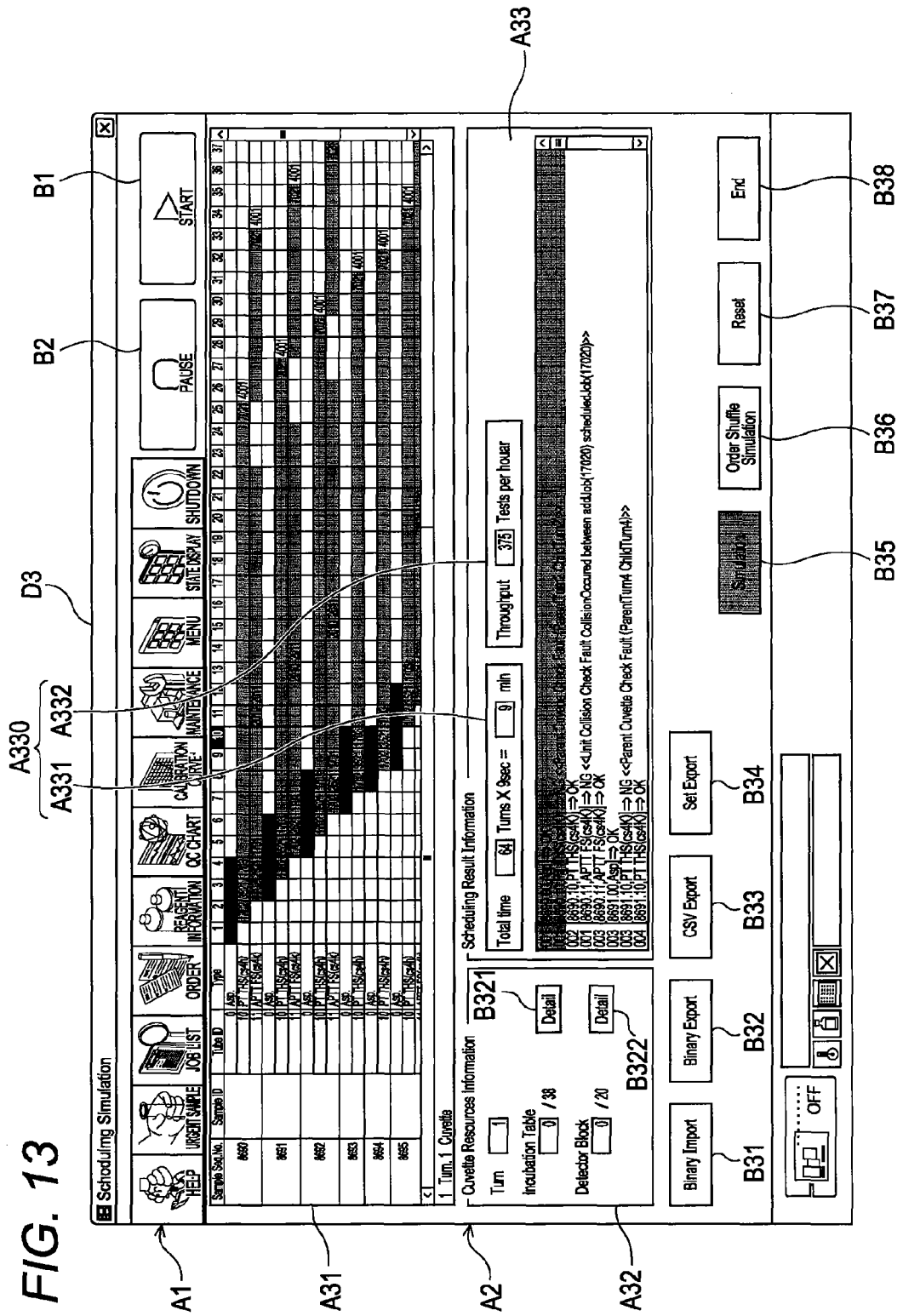
FIG. 13 is a view showing another example of the measurement simulation screen of the sample analyzer according to the first embodiment.

The CPU 401 displays the result of the measurement simulation on the display unit 409 (step S208). FIG. 13 is a view showing another example of the measurement simulation screen. In FIG. 13, the measurement simulation screen in a state the measurement simulation is executed is shown. As shown in the figure, the timing chart of the created sample measurement schedule is displayed in the schedule table display region A31 after the measurement simulation is executed. The throughput information A330 including the total processing time A331 and the average number of processing tests A332 per unit time is displayed in the schedule result display region A33. The log of the schedule creation in the measurement simulation process is displayed at the lower side of the throughput information A330.

Each turn of the timing chart displayed in the schedule table display region A31 can be selected with the mouse, where when one turn is selected, the number of cuvettes set in the warming table 16 and the detection unit 40 in the relevant turn is displayed in the cuvette information display region A32. Furthermore, the cuvette information display region A32 includes the button B321 for displaying in detail the usage status of the warming table 16 estimated by the measurement simulation and the button B322 for displaying in detail the usage status of the detection unit 40 estimated by the measurement simulation.

Figure 14:
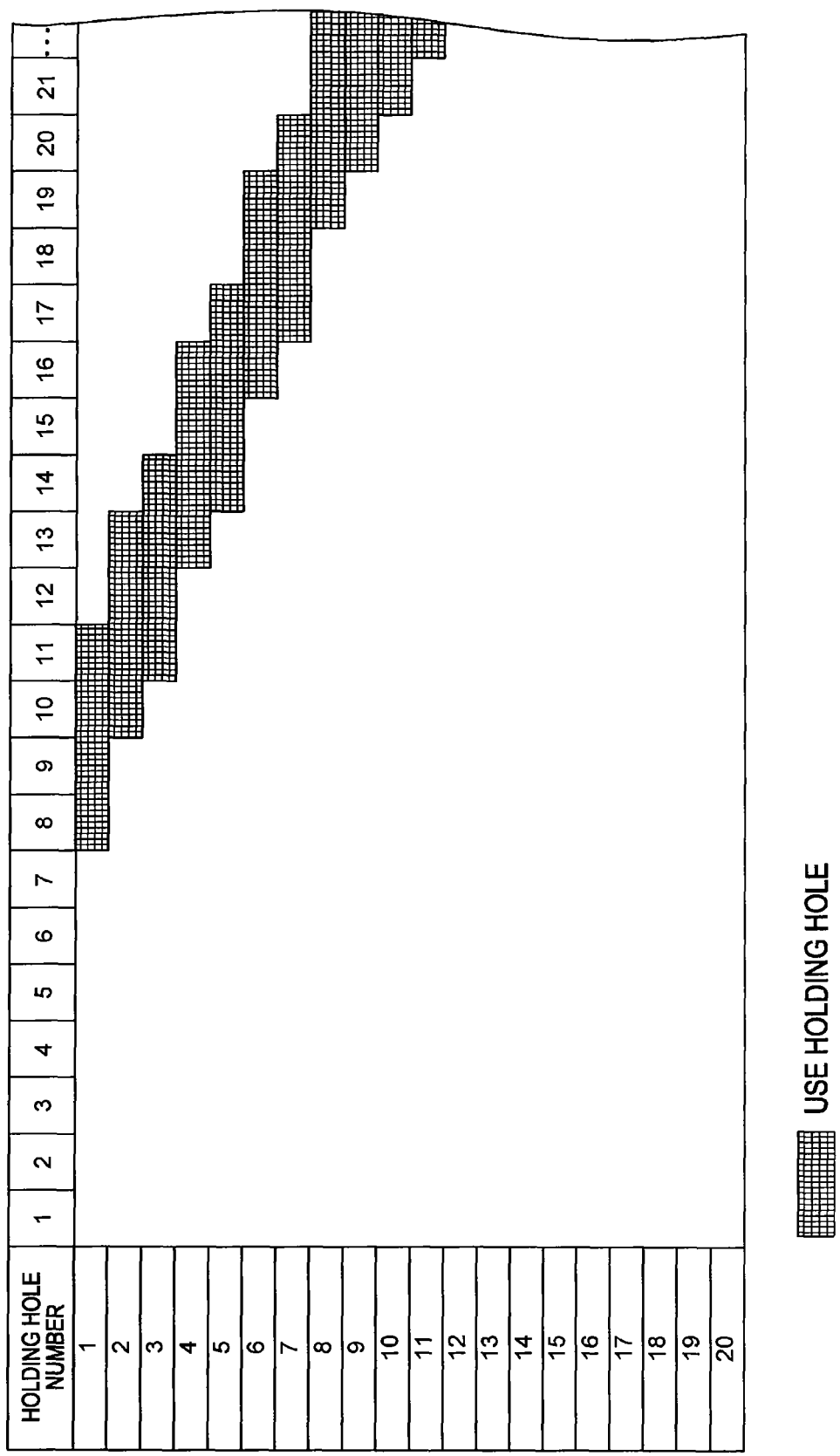
FIG. 14 is a view showing one example of the timing chart showing the usage status of each holding hole of the detection unit.

The buttons B321 and B322 are selection graphical user interface objects. When the button B321 is selected by the click operation of the mouse, a dialogue screen displaying in detail the usage status of the warming table 16 estimated by the measurement simulation is displayed. When the button B322 is selected by the click operation of the mouse, a dialogue screen displaying in detail the usage status of the detection unit 40 estimated by the measurement simulation is displayed. The usage statuses of each cuvette holding hole 16a of the warming table 16 and each holding hole 41 of the detection unit 40 are displayed in a timing chart form in the usage status dialogue screen. FIG. 14 is a view showing one example of the timing chart showing the usage status of each holding hole 41 of the detection unit 40. In the relevant timing chart, each usage status of each holding hole is displayed for every row, and the turn that is not used and the turn that is used are color displayed so as to be distinguishable.

In step S209, the CPU determines whether or not the button B37 is selected, that is, whether or not the initialization of the display of the measurement simulation screen D3 is instructed (step S209). If the initialization of the display of the measurement simulation screen D3 is instructed (YES in step S209), the CPU 401 initializes the display of the measurement simulation screen D3 (step S210), and returns the process to step S202.

If the initialization of the display of the measurement simulation screen D3 is not instructed in step S209 (NO in step S209), the CPU 401 determines whether or not the button B38 is selected, that is, whether or not the termination of the sample throughput estimating process is instructed (step S211). If the termination of the sample throughput estimating process is not instructed (NO in step S211), the CPU 401 returns the process to step S209. If the instruction to terminate the sample throughput estimating process is received in step S211 (YES in step S211), the CPU 401 terminates the process.

Figure 15:
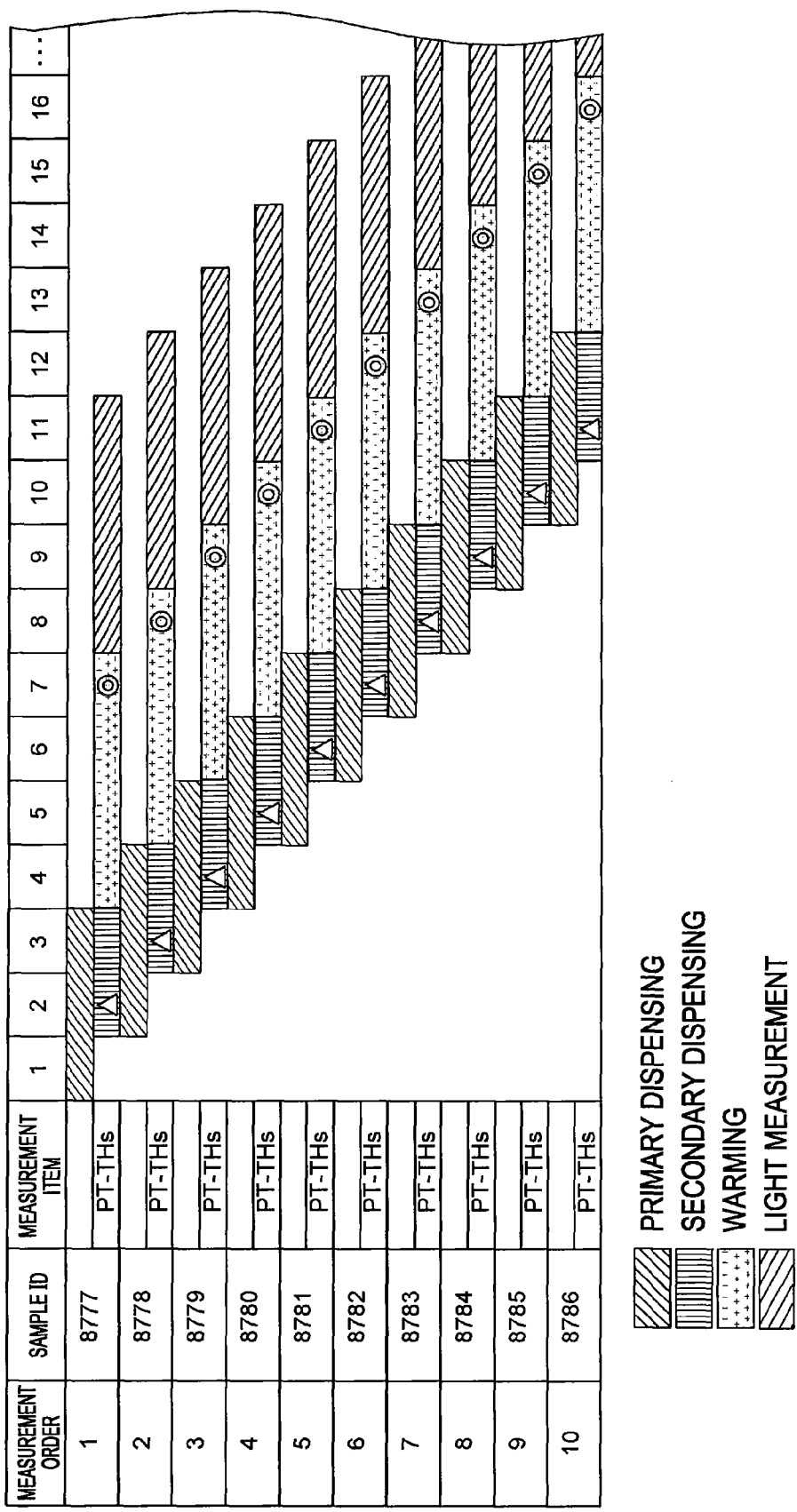
FIG. 15 is a timing chart showing the sample measurement schedule when only the measurement item PT is contained in the measurement order.
Figure 16:
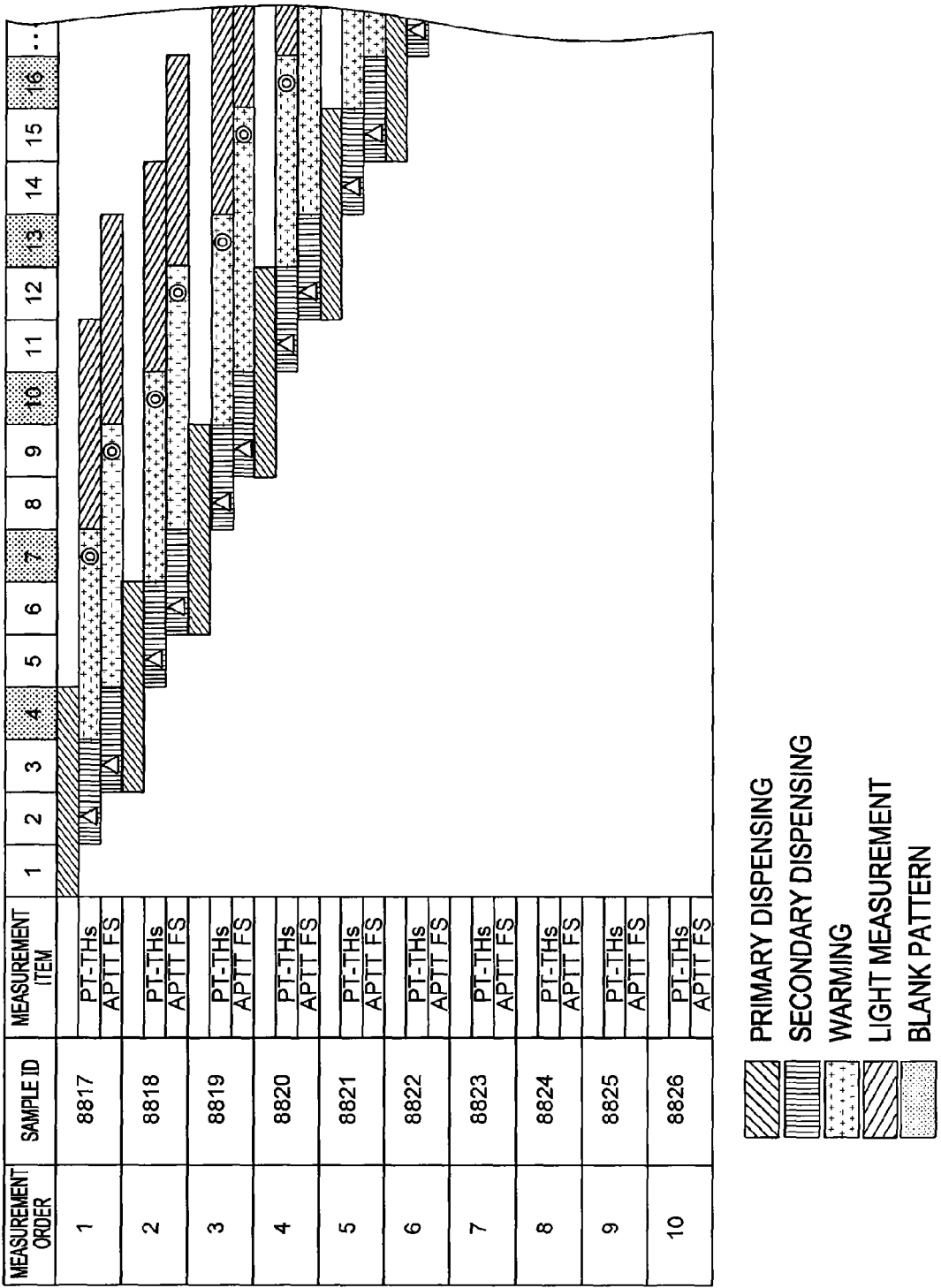
FIG. 16 is a timing chart showing the sample measurement schedule when the measurement items PT and APTT are contained in the measurement order.

The results of the measurement simulation process described above will be described. FIG. 15 is a timing chart showing the sample measurement schedule when only the measurement item PT is contained in the measurement order, and FIG. 16 is a timing chart showing the sample measurement schedule when the measurement items PT and APTT are contained in the measurement order. In the example shown in FIG. 15, the schedule is created such that the sample dispensing operation of the second sample dispensing unit 22 in the secondary dispensing of the sample (shown with Δ mark in the figure) is executed in all turns after the third turn, and the dispensing operation of the trigger reagent in warming the sample (shown with ⊚ mark in the figure) is executed in all turns after the seventh turn. In the example shown in FIG. 15, a blank turn in which the sample dispensing operation in the secondary dispensing and the dispensing operation of the trigger reagent in warming the sample are not executed does not form, and hence the number of total turns becomes a minimum. The throughput estimated in this case is maximum throughput (400 tests/hour) by the sample analyzer 1.

In the example shown in FIG. 16, on the other hand, the protocol differs depending on the measurement item such as four turns are necessary for the warming of the PT, five turns are necessary for the warming of the APTT, and the like. Therefore, in the example shown in FIG. 15, a turn in which the same mechanism portion is used in two or more operations produces if the schedule is created such that the same sample measurement operation is repeatedly executed for every one turn. For instance, the schedule of the PT of the sample with the sample ID "8818" in FIG. 16 is started two turns later than the schedule of the APTT of the sample with the sample ID "8817". This is because, if the schedule of the PT of the sample with the sample ID "8818" is started one turn later than the schedule of the APTT of the sample with the sample ID "8817", the dispensing operation of the trigger reagent is assigned overlapped in the same turn, and hence the schedule of the PT of the sample with the sample ID "8818" is delayed one more turn. Therefore, the throughput estimated in the example shown in FIG. 16 becomes a value (275 tests/hour) lower than the example shown in FIG. 15. In the timing chart of the schedule shown in FIG. 16, the blank turn in which delay occurred is color displayed from other turns to be specifiable in the display region of the turn number of the uppermost level. As the timing chart is displayed in the measurement simulation screen D3, the user can easily specify whether or not the blank turn produced and which turn is the blank turn if produced. Furthermore, as the detailed schedule of the sample measurement operation is shown in the timing chart, the user can easily check for what reasons the blank turn produced by checking the timing chart.

Figure 17:
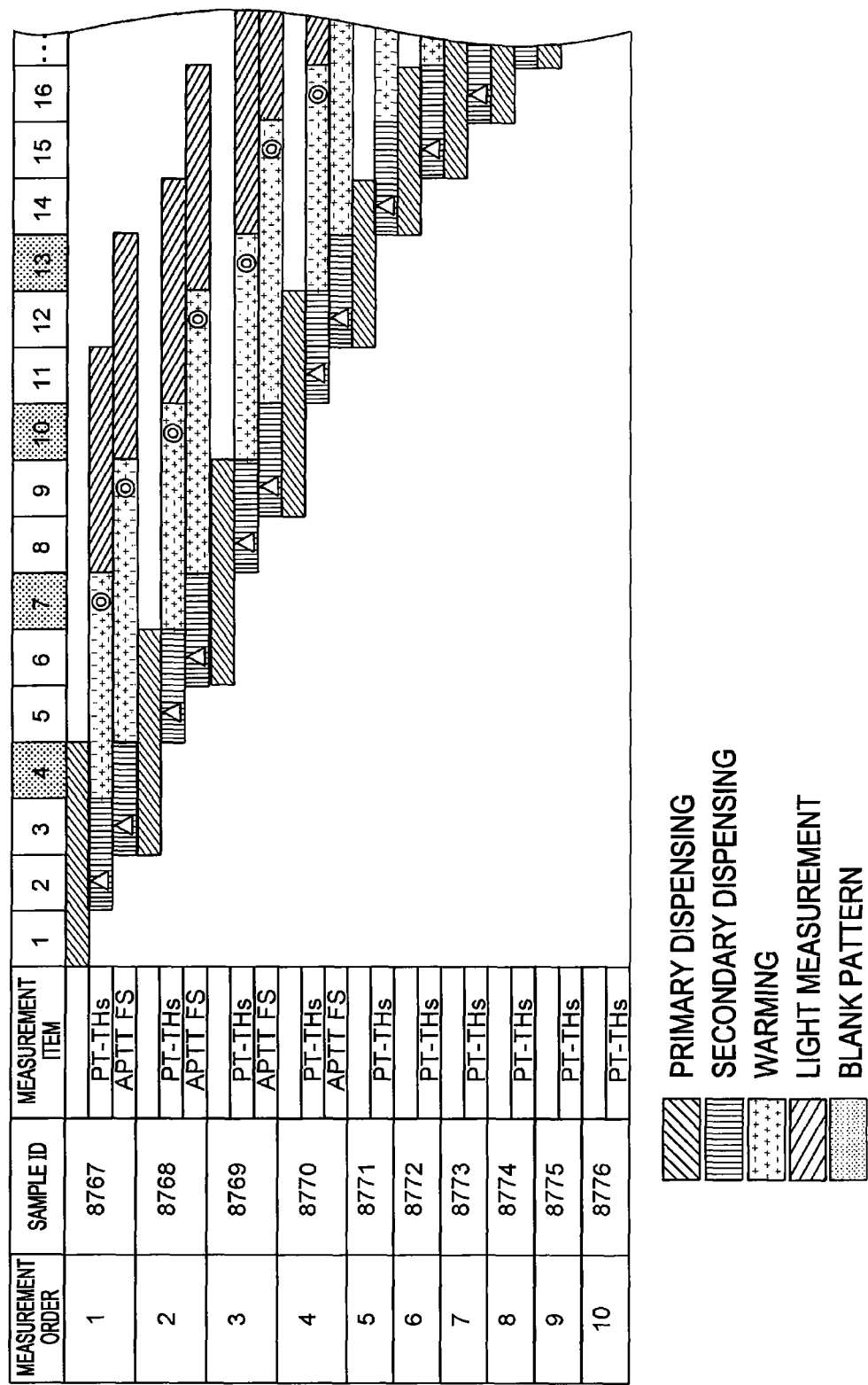
FIG. 17 is a timing chart showing the sample measurement schedule when measuring four samples, in which the measurement items PT and APTT are instructed, first and then measuring six samples, in which only the measurement item PT is instructed, afterwards.
Figure 18:
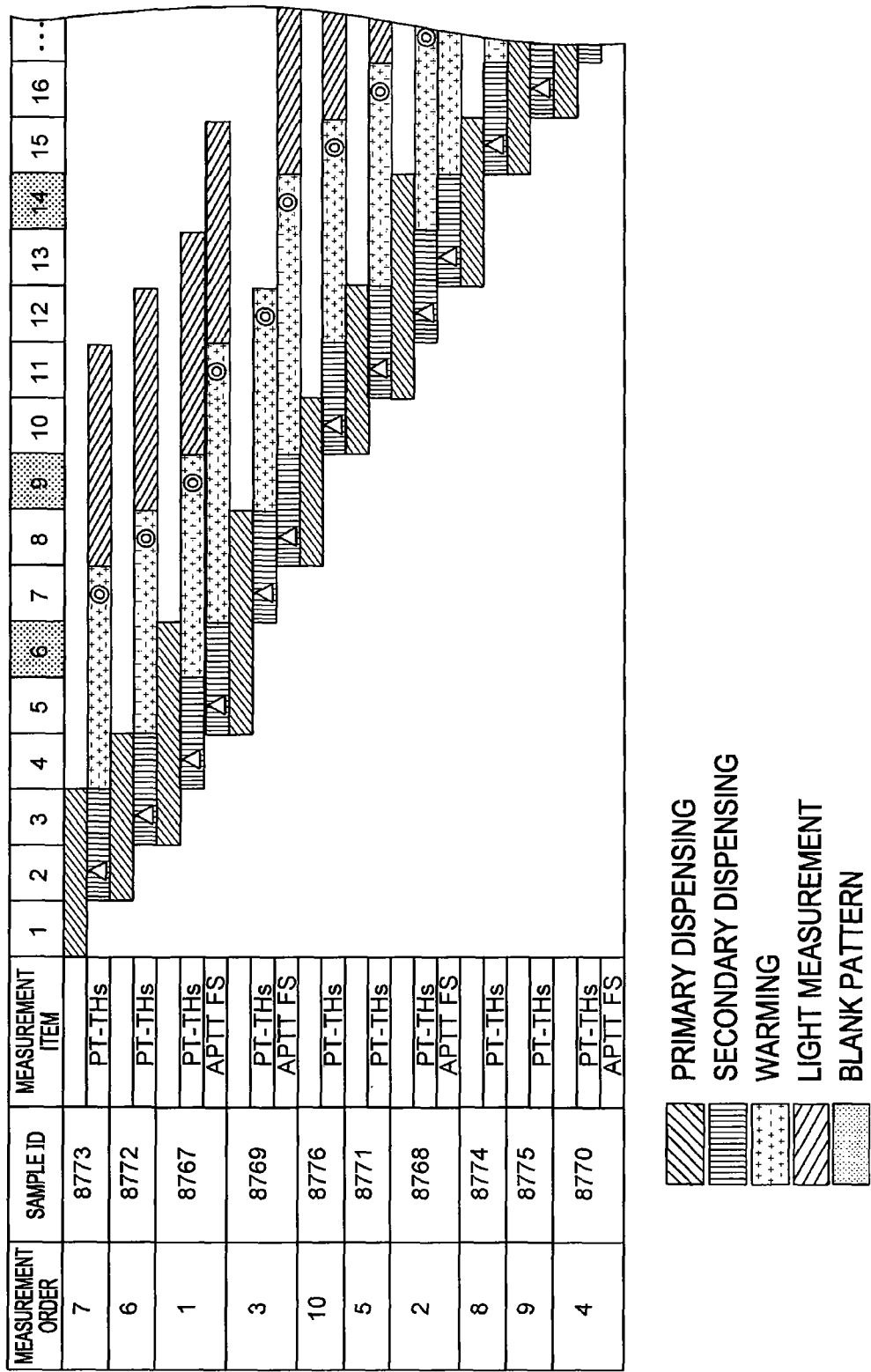
FIG. 18 is a timing chart showing the sample measurement schedule when the measurement order of the samples of FIG. 17 is changed.

The difference in the simulation result due to the difference in the measurement order of the sample will now be described. FIG. 17 is a timing chart showing the sample measurement schedule when measuring four samples, in which the measurement items PT and APTT are instructed, first and then measuring six samples, in which only the measurement item PT is instructed, afterwards, and FIG. 18 is a timing chart shown in the sample measurement schedule when the measurement order of the samples is changed. In the example of FIG. 17, the schedule is adjusted to prevent the turn in which the same mechanism portion is used in two or more operations, and as a result, the throughput lowers, similar to the example shown in FIG. 16. Specifically, delay occurs by one turn in each schedule of the PT of the sample with the sample ID "8768", "8769" "8770", and "8771", and as a result, a loss of four turns produces in the entire schedule. Therefore, in the example of FIG. 17 the estimated value of the throughput becomes 311 tests/hour.

In the measurement order of the example shown in FIG. 17, the result of when the order shuffle simulation is executed is shown in FIG. 18. In the example shown in FIG. 18, the number of times the measurement of PT is carried out after the measurement of APTT is three times, which is one less than the example shown in FIG. 17. As a result, the loss of the turn is one less. Therefore, the estimated value of the throughput becomes 329 tests/hour in the example of FIG. 18, and an estimated value different from the example of FIG. 17 is obtained.

In the sample analyzer 1 according to the present embodiment, the accurate throughput of the sample analyzer 1 can be estimated in view of the interference of the mechanism portion as in the actual measurement operation of the sample analyzer 1.

Even if the measurement order is simply input when the measurement order of the same measurement item is continuously input as in the example shown in FIG. 17, the measurement order of the measurement order can be changed by the order shuffle simulation, so that the simulation result close to the actual measurement operation in which the sample is measured in a random order can be obtained.

Second Embodiment

[Configuration of Sample Analyzer]

The configuration of a sample analyzer according to a second embodiment is similar to the configuration of the sample analyzer according to the first embodiment, and thus the same reference numerals are denoted for the same configuring elements, and the description thereof will be omitted.

[Operation of Sample Analyzer]

The operation of the sample analyzer 1 according to the present embodiment will be described below. The analyzing procedure of the sample is similar to the sample analyzer of the first embodiment, and thus the description thereof will be omitted.

<Throughput Estimating Operation>

The sample analyzer 1 according to the second embodiment can execute the throughput estimating operation of estimating the throughput of the sample analyzer 1. The throughput estimating operation is realized by having the CPU 401 of the information processing device 3 execute the sample throughput estimating process to be described below.

The menu screen of the sample analyzer 1 according to the present embodiment is similar to the menu screen (see FIG. 5) described in the first embodiment. The display screen of the information processing device 3 according to the present embodiment all commonly includes the tool bar A1 and the work region A2, similar to the first embodiment, where the display content of the work region A2 differs by the display screen. The tool bar A1 includes buttons for calling out functions used frequently such as a start button B1 for instructing the start of sample measurement and a pause button B2 for pausing the sample measurement.

In order to cause the sample analyzer 1 according to the second embodiment to execute the throughput estimating operation, the service man needs to log into the sample analyzer 1 and select the icon SS (see FIG. 5) displayed in the menu screen D1, similar to the first embodiment.

Figure 19:
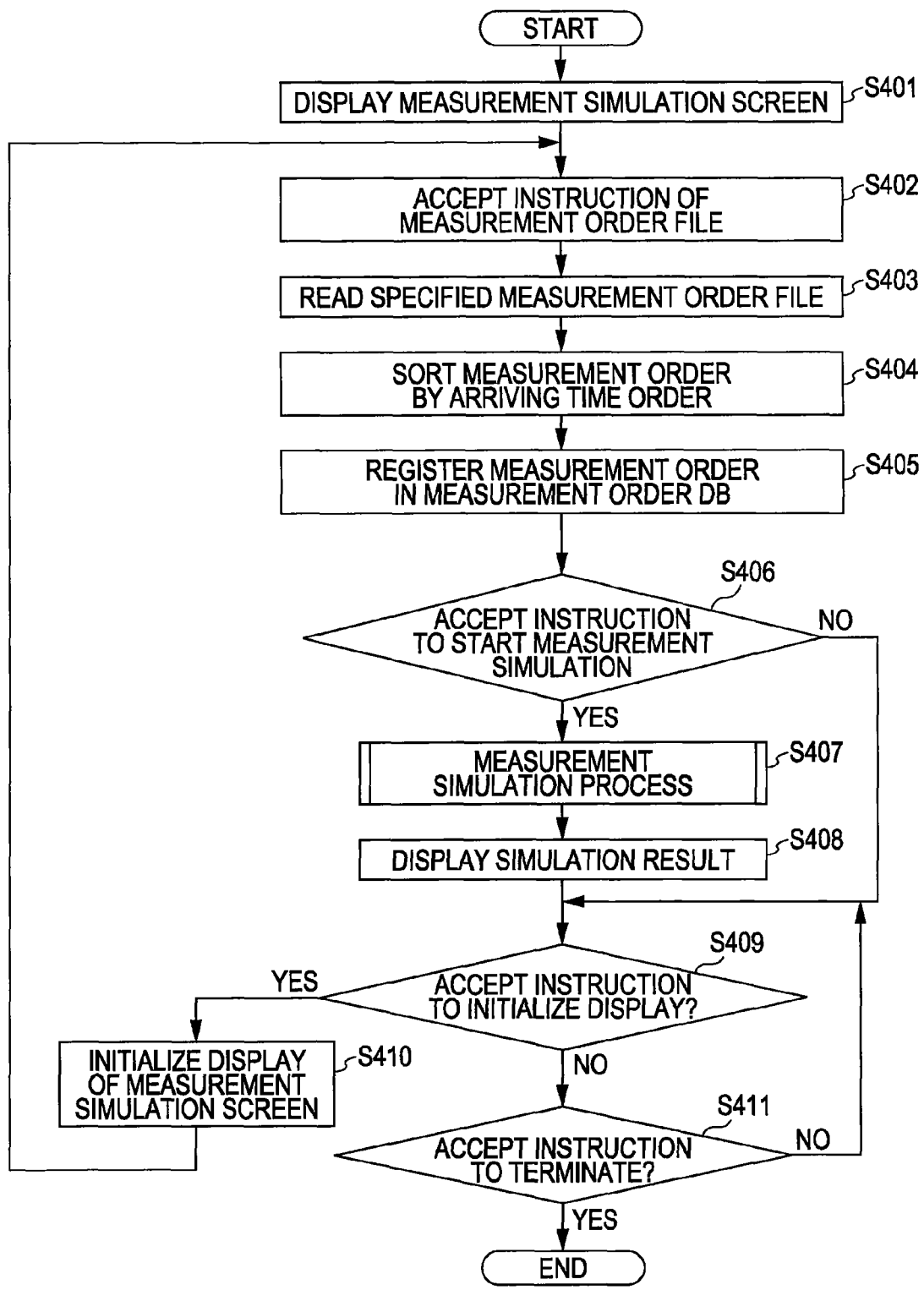
FIG. 19 is a flowchart showing the procedure of the sample throughput estimating process of the sample analyzer according to a second embodiment.

FIG. 19 is a flowchart showing the procedure of the sample throughput estimating process of the sample analyzer according to the second embodiment. The CPU 401 receives the execution instruction of the sample throughput estimating process from the user with the menu screen D1 displayed. When the user operates the input unit 408 and selects the icon SS to instruct the information processing device 3 to execute the sample throughput estimating process, the CPU 401 starts the sample throughput estimating process and displays the measurement simulation screen on the display unit 409 (step S401).

Figure 20:
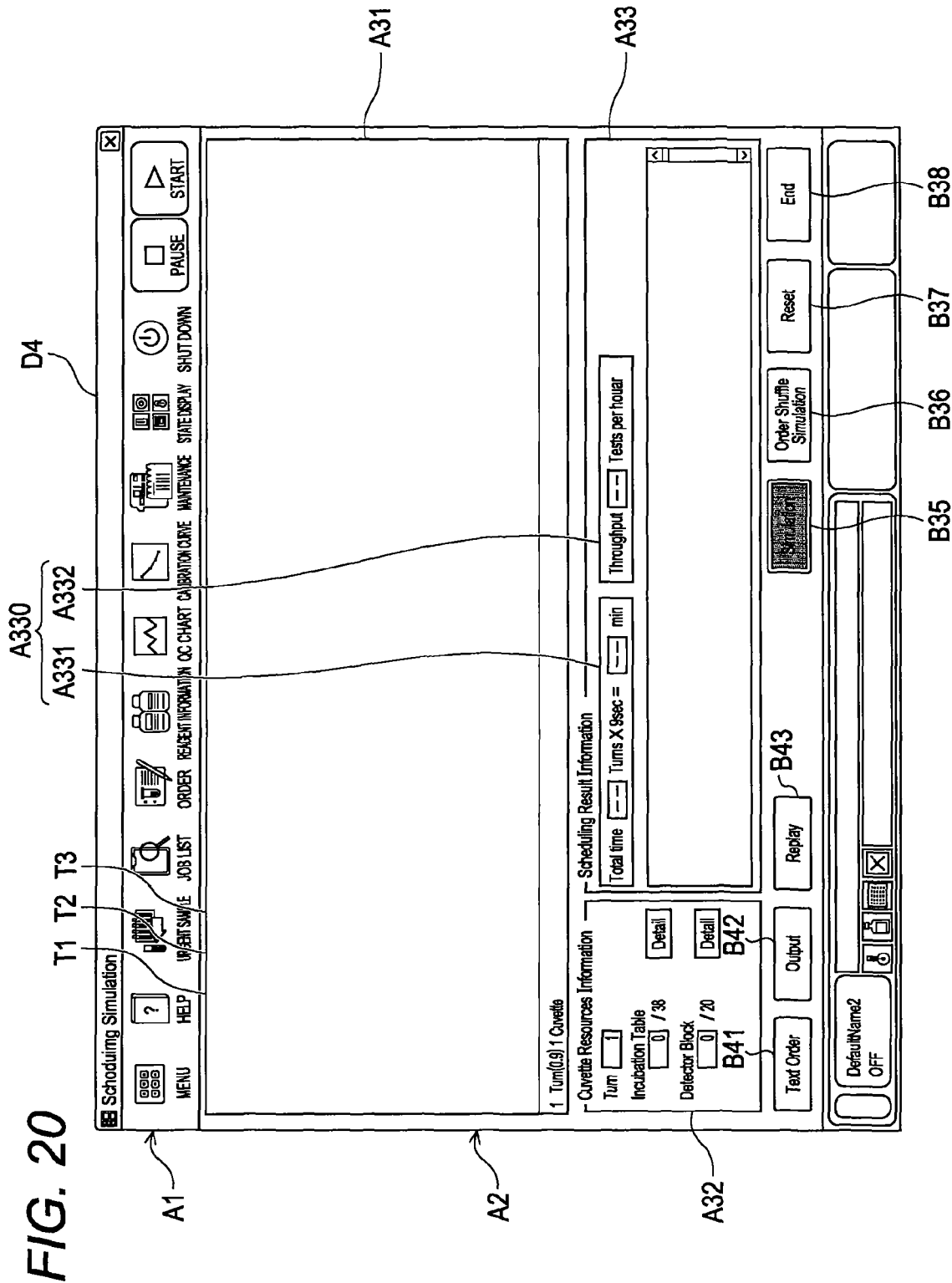
FIG. 20 is a view showing one example of a measurement simulation screen of the sample analyzer according to the second embodiment.

FIG. 20 is a view showing one example of a measurement simulation screen. In FIG. 20, the measurement simulation screen in a state the measurement simulation is not executed is shown. The work region A2 of the measurement simulation screen D4 includes a schedule table display region A31 for displaying the schedule of the sample measurement created by the measurement simulation in a timing chart form. At the lower side of the schedule table display region A31, a cuvette information display region A32 for displaying the usage status of the warming table 16 and the detection unit 40 obtained by the measurement simulation, and a schedule result display region A33 for displaying throughput information A330 including a total processing time A331 obtained by the measurement simulation and an average number of processing tests A332 per unit time are arranged. Nothing is displayed in the schedule table display region A31, the cuvette information display region A32, and the schedule result display region A33 before the measurement simulation is executed.

The buttons B41 to 43 and B35 to B38, which are selection graphical user interface objects, are arranged on the lower side of the cuvette information display region A32 and the schedule result display region A33 of the work region A2.

The information processing device 3 according to the present embodiment is configured so that the file of the measurement order in CSV format can be input. The button B41 is a button for reading the measurement order file of the CSV format. When the button B41 is selected, a dialogue (not shown) for specifying the measurement order file to be input is displayed on the display unit 409. In this dialogue, the folder in which the measurement order file is stored and the measurement order file to be read can be specified.

FIG. 21 is a schematic view showing one example of the content of a measurement order file. The measurement order file MOF is a file of CSV format and thus one measurement order is described in one row. The measurement order file includes a column C401 of the sample ID, a column C402 of the arriving time of the sample, and columns C403, C404, C405, C406, C407, C408 . . . of the measurement items. Here, the "arriving time" refers to the time the sample is set in the pre-analysis rack holding region of the sample analyzer 1. The sample may go through various steps before the sample is analyzed by the sample analyzer 1. For instance, since the sample to be inspected by the sample analyzer 1 is blood plasma, the blood plasma needs to be extracted from the whole blood by a centrifuge separator. Normally, a plurality of samples is collectively processed by the centrifuge separator, and hence the plurality of samples which are completed with the process by the centrifuge separator are set in the pre-analysis rack holding region of the sample analyzer 1 all at once. Furthermore, the sample is sometimes provided to other sample tests such as biochemical test, immune test, blood cell counting test and the like before the blood coagulation test by the sample analyzer 1. In such a case, each sample is transported to the sample analyzer 1 after other sample test is terminated, and each sample separately arrives at the sample analyzer or collectively arrives at the sample analyzer all together. Therefore, the process performed on the sample before the blood coagulation test differs depending on the facility, and the timing at which the sample arrives at the sample analyzer 1 also varies by facilities. The arriving time can be specified for every sample in the measurement order file MOF. The user creates the measurement order file MOF in which the arriving time of each sample corresponding to the facility of the user is specified. In the example of FIG. 21, the arriving time is specified such that each sample having the sample ID "Test1" to "Test10" arrives every one minute from 9:00, each sample "Test11" to "Test25" arrives all together at 10:00, each sample "Test26" to "Test29" arrives all together at 11:00, and the sample "Test30" arrives at 12:00.

As shown in FIG. 21, the measurement item of the sample is specified by inserting "*" to the corresponding cell. In the example of FIG. 21, "PT" and "APTT" are specified for the measurement item of the sample having the sample ID "Test1", and "PT" is specified for the measurement item of the sample having the sample ID "Test5".

The user specifies the above described measurement order file in the dialogue. The specified measurement order file thus can be read out by the information processing device 3.

The button B42 is a button for saving (outputting) the result of the measurement simulation displayed. When the button B42 is selected, the measurement simulation result saving dialogue (not shown) is displayed, so that the user can specify the folder of the output destination, the file name, and the file format (CSV or binary) in the relevant dialogue. When the output of the measurement simulation result is instructed in the measurement simulation result saving dialogue, the measurement simulation result file including the information of each sample, the sample ID, the measurement mode, the measurement item, the arriving time of each sample, the result acquiring time (measurement complete time), time (waiting time) from the arrival of the sample to the acquisition of the result, the average number of processing tests per unit time, and the total processing time is output. The button B43 is a button for reading an output file of binary form indicating the results of the past measurement simulation, and redisplaying the results of the measurement simulation.

The buttons B35 to B38 are similar to the buttons B35 to B38 described in the first embodiment, and the description thereof will be omitted.

In the present embodiment described above, the file of the measurement order can be input from the measurement simulation screen described above. The CPU 401 receives the specification of the measurement order file in the above manner (step S402). When receiving the specification of the measurement order file, the CPU 401 reads out the specified measurement order file (step S403). The CPU 401 sorts the read measurement order in the arriving time order (step S404). In this process, if the measurement order in which the arriving time is not specified exists, such measurement order is handled as arriving at the earliest arriving time. After the process of step S404 is completed, the CPU 401 registers the input measurement order in the measurement order database of the hard disc 404 (step S405).

The user then selects the button B35 of the measurement simulation screen D4 when desiring to know the throughput of the sample analyzer 1 for the registered measurement order as described above. The CPU 401 determines whether or not the selection of the button B35 is received, that is, whether or not the instruction to start the measurement simulation by the registered measurement order is received (step S406). The CPU 401 executes the measurement simulation process (step S407) when receiving the instruction to start the measurement simulation (YES in step S406). If the instruction to start the measurement simulation is given in step S406, the measurement simulation is executed assuming the sample arrived at the arriving time of each measurement order. The CPU 401 proceeds the process to step S409 on the other hand when not receiving the instruction to start the measurement simulation in step S406 (NO in step S406).

Figure 22:
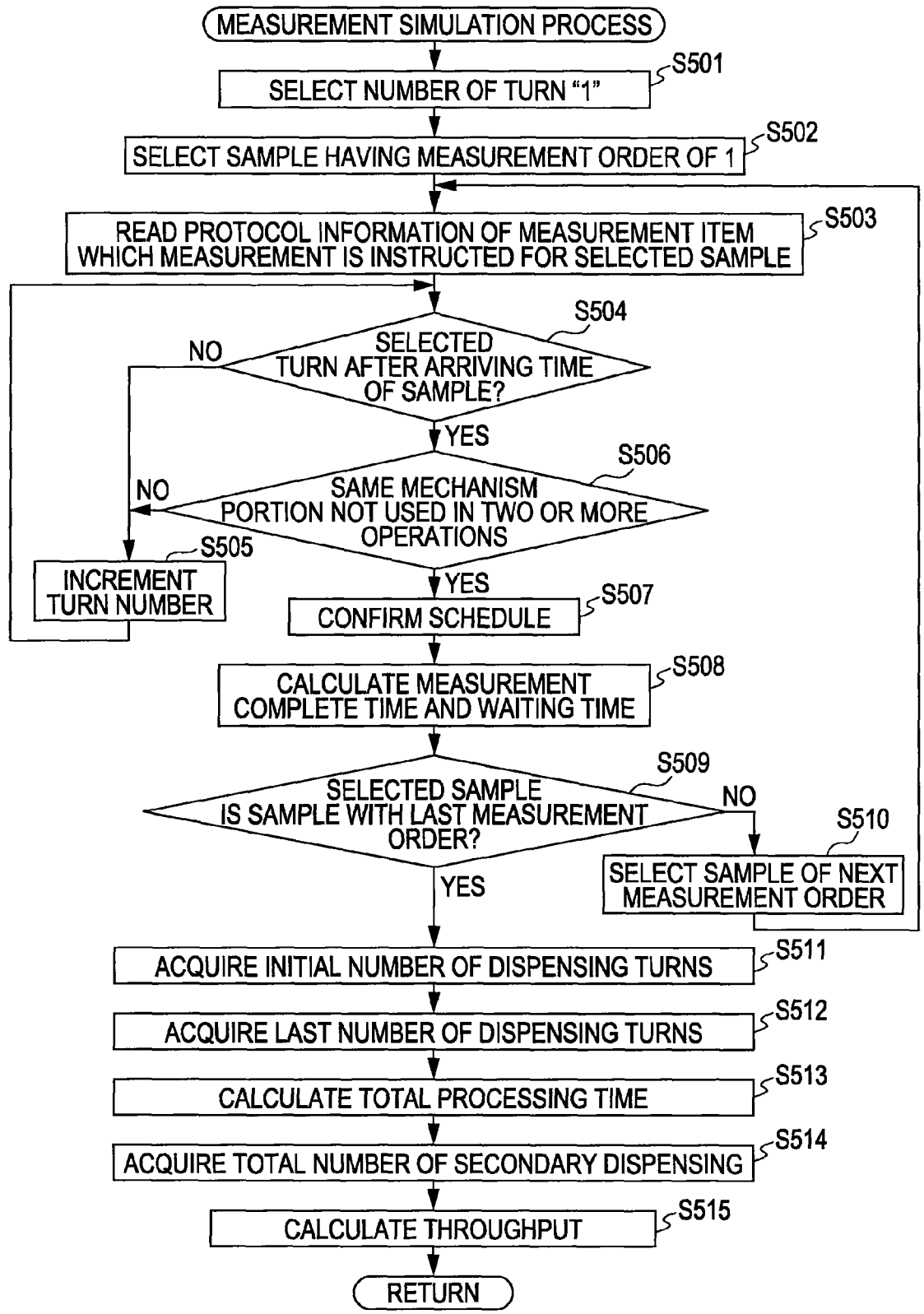
FIG. 22 is a flowchart showing a procedure of the measurement simulation process of the sample analyzer according to the second embodiment.

The measurement simulation process according to the present embodiment will now be described in detail. FIG. 22 is a flowchart showing a procedure of the measurement simulation process according to the present embodiment. In the measurement simulation process, the CPU 401 first selects "1" for the initial value of the turn number (step S501) and selects the sample having the measurement order of 1 in the registered measurement order (step S502).

The CPU 401 then specifies the measurement item to which measurement is instructed for the selected sample, and reads out the protocol information for such measurement item from the hard disc 404 (step S503). The CPU 401 then determines whether or not the turn number selected at this time point is after the arriving time of the sample specified in the input measurement order file (step S504). In this process, the time of turn number "1" or the first turn is the earliest time of the arriving times of the samples specified in the measurement order file. That is, if the turn number "1" is selected, determination is always made as coinciding with the arriving time of the selected sample (sample having measurement order of 1). If the selected turn number is "5", and the time corresponding to such turn is "9:10", determination is made that the relevant turn is not after the arriving time in step S504 if the sample which arriving time is "9:11" is selected. If the sample which arriving time is "9:11" is selected and the time corresponding to the selected turn number of "6" is "9:11", determination is made that the relevant turn is after the arriving time. Furthermore, if the time corresponding to the selected turn number is later than the arriving time, for instance, if the arriving time is "9:11" and the time corresponding to the selected turn number is "9:20", determination is made that the relevant turn is after the arriving time.

If determined that the selected turn is not after the arriving time in step S504 (NO in step S504), the CPU 401 increments the turn number by one (step S505) and returns the process to step S504.

If determined that the selected turn is after the arriving time in step S504 (YES in step S504), the CPU 401 references the schedule for the sample that is already confirmed, and determines whether or not the same mechanism portion is used in two or more operations in the same turn in the relevant schedule and another confirmed schedule (step S506). If determined that the same mechanism portion is used in two or more operations in the same turn in step S506 (NO in step S506), the CPU 401 increments the turn number by 1 (step S505), and returns the process to step S504.

If determined that the same mechanism portion is not used in two or more operations in the selected turn in step S506 (YES in step S506), the CPU 401 confirms the schedule of the sample so as to start from the selected turn (step S507), and calculates the measurement complete time (time corresponding to last turn of schedule) and the waiting time (time from arriving time until measurement complete time) of the sample (step S508). The CPU 401 then determines whether or not the selected sample is the last sample in the measurement order (step S509), and selects the sample of next measurement order (step S510) if not the last sample (NO in step S509) and returns the process to step S503.

If the last sample in the measurement order is selected in step S509 (YES in step S509), the CPU 401 proceeds the process to step S511. The processes of steps S511 to S515 are similar to the processes of steps S306 to S310 described in the first embodiment, and thus the description thereof will be omitted. After the process of step S515 is completed, the CPU 401 returns the process to the callout address of the measurement simulation process in the sample throughput estimating process.

Figure 23:
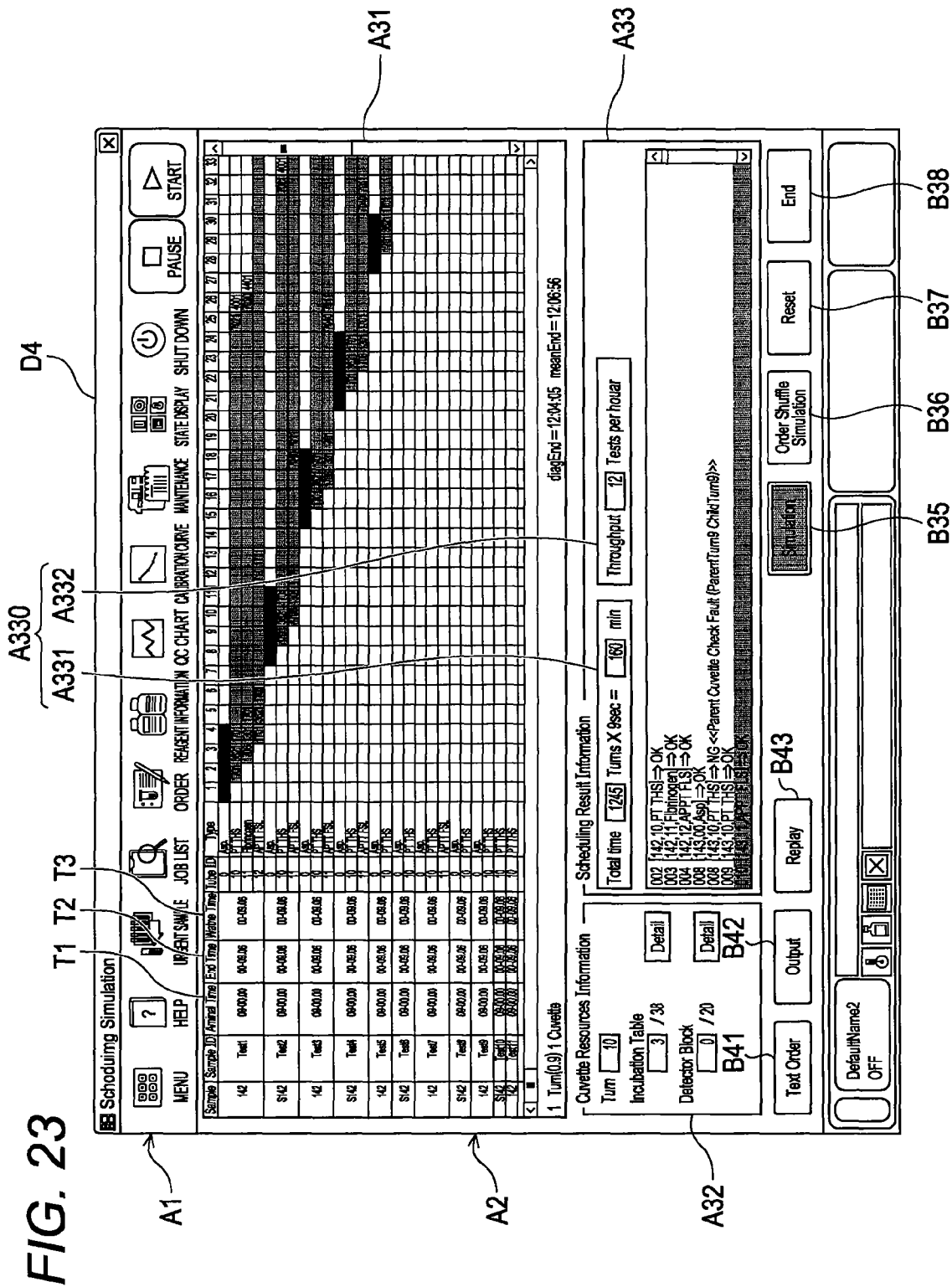
FIG. 23 is a view showing another example of the measurement simulation screen of the sample analyzer according to the second embodiment.

The CPU 401 displays the result of the measurement simulation on the display unit 409 (step S408). FIG. 23 is a view showing another example of the measurement simulation screen. In FIG. 23, the measurement simulation screen in a state the measurement simulation is executed is shown. As shown in the figure, the timing chart of the created sample measurement schedule is displayed in the schedule table display region A31 after the measurement simulation is executed. The throughput information A330 including the total processing time A331 and the average number of processing tests A332 per unit time is displayed in the schedule result display region A33. The log of the schedule creation in the measurement simulation process is displayed at the lower side of the throughput information A330. In the timing chart of the schedule table display region A31, the arriving time T1 of the sample, the measurement complete time T2, and the waiting time T3 are displayed in correspondence with the schedule of each sample. The user thus can check the arriving time T1 of each sample and determine the validity of the arriving time T1 on the measurement simulation screen. For instance, if the arriving time used in the measurement simulation does not correspond to the actual operation of the relevant facility, the user can again create the measurement order file in which the arriving time is corrected, and redo the measurement simulation based thereon. Furthermore, in the screen, the font color of the waiting time T3 is changed for display according to the length of the waiting time T3. Specifically, T3 is displayed in a black font color if T3<15 minutes, T3 is displayed in yellow font color if 15 minutes≤T3<30 minutes, and displayed in red font color if 30 minutes≥T3. The sample with long waiting time then can be easily found. All the samples displayed in FIG. 23 have the waiting time T3 of less than 15 minutes, and thus are all displayed in black font color. Furthermore, since the measurement complete time T2 and the waiting time T3 are displayed in the measurement simulation result, the user can check when each sample completes the measurement or how much time is required from the start to the completion of the measurement of each sample. For instance, when considering newly introducing the sample analyzer to the facility, whether such sample analyzer is usable in the relevant facility can be accurately evaluated if what extent of time the measurement is completed and how much time is required from the start to the completion of the measurement at the arriving time of the sample actually operated in the facility are known. Therefore, according to the throughput estimating function of the sample analyzer 1 according to the present embodiment, the information on the measurement completion time and the waiting time of each sample useful when considering the introduction of the sample analyzer can be provided to the user.

In step S409, the CPU 401 determines whether or not the initialization of the display of the measurement simulation screen is instructed (step S409). If the initialization of the display of the measurement simulation screen is instructed (YES in step S409), the CPU 401 initializes the display of the measurement simulation screen (step S410), and returns the process to step S402.

If the initialization of the display of the measurement simulation screen is not instructed in step S409 (NO in step S409), the CPU 401 determines whether or not the termination of the sample throughput estimating process is instructed (step S411). If the termination of the sample throughput estimating process is not instructed (NO in step S411), the CPU 401 returns the process to step S409. If the instruction to terminate the sample throughput estimating process is received in step S411 (YES in step S411), the CPU 401 terminates the process.

Therefore, in the sample analyzer 1 according to the present embodiment, the measurement simulation can be carried out while specifying the arriving time of the sample adapted to the operation of the facility, and thus an accurate simulation result when the sample analyzer 1 is actually introduced to the facility can be obtained. Therefore, when considering to newly introduce the sample analyzer to the facility, the accurate simulation when the sample analyzer is introduced to the relevant facility can be carried out and the user can use the simulation result as assistance information for determining on the introduction of the sample analyzer.

Other Embodiments

In the first and second embodiments, the configuration in which the throughput estimating process is executed by the information processing device 3 of the sample analyzer 1 has been described, but this is not the sole case. The throughput estimating process may be executed by a throughput information generating device configured separate from the sample analyzer. The information throughput estimating process may be executed by the server device configured by a computer, the processing result may be transmitted from the server device to the client device connected to the server device through the network, and the client device may display the processing result. A dispersed system in which the functions of the information processing device 3 are carried out in a dispersed manner in a plurality of computers may be adopted.

In the first and second embodiments, the configuration of outputting the total processing time and the average number of tests processed per one hour as information indicating the throughput has been described, but this is not the sole case. The total processing time and the total number of secondary dispensing may be output for the information indicating the throughput.

In the first and second embodiments, the configuration of calculating the average number of processing tests per unit time with an equation has been described, but this is not the sole case. A lookup table showing the relationship of the total number of secondary dispensing in the created sample measurement schedule, that is, the number of optical measurements (number of samples divided by secondary dispensing) by the detection unit 40 and the total processing time, and the value of the corresponding throughput may be stored in the hard disc 404, and the average number of processing tests per unit time may be acquired by referencing the lookup table when the total number of secondary dispensing and the total processing time are obtained, and then output.

In the first and second embodiments, the configuration in which the sample analyzer 1 is the blood coagulation measurement apparatus, and the throughput of the sample analyzer 1 or the blood coagulation measurement apparatus is estimated by the information processing device 3 has been described, but this is not the sole case. The sample analyzer may be a sample analyzer other than the blood coagulation measurement apparatus such as a blood cell counting apparatus, an immune analyzer, a urine formed element analyzer or a urine qualitative analyzer, and the throughput of such sample analyzer may be estimated by the information processing apparatus 3, or the throughput of the sample analyzer (e.g., blood cell counting apparatus when sample analyzer 1 is blood coagulation measurement apparatus) of a type different from the sample analyzer may be estimated by the information processing device 3 of the sample analyzer 1. In this case, the type of sample analyzer of a target for estimating the throughput can be selected by the user, and the throughput of the sample analyzer selected by the user can be estimated by the information processing device.

In the first and second embodiment, an example of inputting one measurement order with respect to one sample has been described, but this is not the sole case. The measurement order may be input for every measurement item. In this case, a plurality of measurement orders is input with respect to one sample.

In the first and second embodiments, information of the protocol of the sample measurement is stored for every measurement item in the hard disc 404. The protocol information stored in the hard disc 404 may be changed by the user as a variant. For instance, the warming time and the light measurement time may be arbitrarily changed. The throughput corresponding to the state for every facility thus can be calculated even if the measurement protocol differs for every facility by enabling the protocol information to be changeable.

In the first and second embodiments, the configuration in which the CPU 401 of the information processing device 3 calculates the total processing time of the sample analyzer by the equation has been described, but this is not the sole case. A lookup table storing the value of the total processing time corresponding to each combination of the initial dispensing turn number and the last dispensing turn number may be provided in the hard disc 404, and the CPU 401 may reference the lookup table to read out the total processing time corresponding to the acquired initial dispensing turn number and the last dispensing turn number to generate information indicating the total processing time.

In the first and second embodiments, the configuration in which the CPU 401 of the information processing device 3 calculates the throughput of the sample analyzer by the equation has been described above, but this is not the sole case. A lookup table storing the value of the throughput corresponding to each combination of the total processing time and the total number of secondary dispensing may be stored in the hard disc 404, and the CPU 401 may reference the lookup table to read out the throughput corresponding to the acquired total processing time and total number of secondary dispensing and generate the information indicating the throughput.

In the second embodiment, the configuration of displaying each of the arriving time, the measurement complete time, and the waiting time in the measurement simulation screen has been described, but this is not the sole case. The arriving time may be displayed and the measurement complete time and the waiting time may not be displayed, or the measurement complete time and the waiting time may be displayed and the arriving time may not be displayed. The arriving time and the measurement complete time may be displayed and the waiting time may not be displayed, or the arriving time and the waiting time may be displayed and the measurement complete time may not be displayed. Only the measurement complete time may be displayed, or only the waiting time may be displayed.

In the second embodiment, the measurement order file in which the arriving time of each sample is specified may be input to the sample analyzer, and the measurement simulation may be executed based on the measurement order specified in the measurement order file has been described, but this is not the sole case. For instance, the arriving time of each sample can be input in the measurement order registration screen in the first embodiment, and the measurement simulation may be executed based on the arriving time and the measurement order specified in the measurement order registration screen.

In the second embodiment, the time at which the sample is set in the pre-analysis rack holding region of the sample analyzer 1 has been described as the "arriving time" by way of example, but this is not the sole case. For instance, the sample analyzer 1 takes a form of being connected to a stock yard in which the sample rack is set and a transport device for transporting the sample from the stock yard to the pre-analysis rack holding region, where the arriving time may be a time at which the sample is set in the stock yard. In this case, the schedule including the time required for the transportation of the sample from the stock yard to the pre-analysis rack holding region may be created.

What is claimed is:

1. A sample analyzer, comprising:
a measurement device that measures a plurality of samples on a plurality of measurement items and comprises a measurement unit, a detection unit, and a transport unit, wherein the measurement device performs measurements of the measurement items of the samples at different timings;
an output device operable to display a menu screen of the sample analyzer;
a controller including a processor and a memory under control of the processor, the processor programmed to carry out instructions comprising:
receiving an input of a plurality of measurement orders, wherein a measurement order includes a designation of at least one measurement item and storing the input as an measurement order file;
prompting to enter an instruction that executes a sample throughput estimation process;
generating a sample measurement schedule that assigns, for each turn, operations of the measurement device with respect to each measurement item of each sample;
wherein according to the sample measurement schedule, the operations of the measurement device are simultaneously executed in parallel to the extent that each mechanism portion of the measurement device is not used in two operations that take place during an identical turn;
upon receipt of the instruction, reading out the measurement order file, sorting the measurement orders in an arriving time order specified in the measurement order file and registering the measurement orders in a database;
executing a measurement simulation of the registered measurement orders by:
selecting a turn number and a sample having a measurement order number corresponding to the selected turn number;
determining whether or not the selected turn number coincides with the arriving time of the sample specified in the measurement order file;
upon determination that the selected turn number coincides with the arriving time, verifying the sample measurement schedule of the sample; and
upon determination of a last measurement order of the sample, calculating a total processing time and throughput information based on the sample measurement schedule; and
outputting a measurement simulation screen on the output device, the measurement simulation screen displaying a timing chart that graphically depicts the sample measurement schedule, the total processing time and the throughput information.

2. The sample analyzer according to claim 1, wherein the arriving time specifies a time at which each sample arrives at the sample analyzer.

3. The sample analyzer according to claim 2, wherein the measurement simulation screen further displays a time required from when the sample arrives at the sample analyzer until the measurement is completed.

4. The sample analyzer according to claim 2, wherein the total processing time specifies a time point where a measurement is completed for each sample.

5. The sample analyzer according to claim 2, wherein the controller is further programmed to display the received arriving time for each sample on the measurement simulation screen.

6. A method of measuring a sample on a plurality of measurement items with a sample analyzer comprising a measurement device, in which measurement time differs from each other; the method comprising the steps of:

receiving an input of a plurality of measurement orders, wherein a measurement order includes a designation of at least one measurement item and storing the input as an measurement order file;

prompting to enter an instruction that executes a sample throughput estimation process;

generating a sample measurement schedule that assigns, for each turn, operations of a measurement device with respect to each measurement item of each sample, wherein according to the sample measurement schedule, the operations of the measurement device are simultaneously executed in parallel to the extent that each mechanism portion of the measurement device is not used in two operations that take place during an identical turn;

upon receipt of the instruction, reading out the measurement order file, sorting the measurement orders in an arriving time order specified in the measurement order file and registering the measurement orders in a database;

executing a measurement simulation of the registered measurement orders by:

selecting a turn number and a sample having a measurement order number corresponding to the selected turn number;

determining whether or not the selected turn number coincides with the arriving time of the sample specified in the measurement order file;

upon determination that the selected turn number coincides with the arriving time, verifying the sample measurement schedule of the sample; and upon determination of a last measurement order, calculating a total processing time and throughput information of the sample analyzer based on the sample measurement schedule; and outputting a measurement simulation screen that displays a timing chart that graphically depicts the sample measurement schedule, the total processing time and the throughput information.

\* \* \* \* \*